United States Patent
Sabelle et al.

(10) Patent No.: US 10,731,038 B2
(45) Date of Patent: *Aug. 4, 2020

(54) (DIS)SYMMETRIC AZOMETHINE-TYPE DIRECT DYE COMPRISING AT LEAST ONE PYRAZOLOPYRIDINE UNIT, PROCESS FOR DYEING KERATIN FIBERS USING THIS DYE

(71) Applicant: L'OREAL, Paris (FR)

(72) Inventors: Stéphane Sabelle, Aulnay-sous-Bois (FR); Stéphane Blais, Aulnay-sous-Bois (FR); Aziz Fadli, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/309,296

(22) PCT Filed: Jun. 21, 2017

(86) PCT No.: PCT/EP2017/065274
§ 371 (c)(1),
(2) Date: Dec. 12, 2018

(87) PCT Pub. No.: WO2017/220670
PCT Pub. Date: Dec. 28, 2017

(65) Prior Publication Data
US 2019/0309170 A1    Oct. 10, 2019

(30) Foreign Application Priority Data
Jun. 23, 2016 (FR) ..................... 16 55866

(51) Int. Cl.
| A61Q 5/10 | (2006.01) |
| C09B 55/00 | (2006.01) |
| A61K 8/49 | (2006.01) |
| C07D 471/04 | (2006.01) |
| C07D 519/00 | (2006.01) |
| C09B 53/02 | (2006.01) |

(52) U.S. Cl.
CPC ............ *C09B 55/003* (2013.01); *A61K 8/494* (2013.01); *A61K 8/4946* (2013.01); *A61Q 5/10* (2013.01); *C07D 471/04* (2013.01); *C07D 519/00* (2013.01); *C09B 53/02* (2013.01); *A61K 2800/432* (2013.01); *A61K 2800/87* (2013.01)

(58) Field of Classification Search
CPC ...... A61Q 5/065; A61K 8/494; C07D 471/04; C09B 69/07; C09B 55/006
See application file for complete search history.

(56) References Cited

U.S. PATENT DOCUMENTS

| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 5,792,221 A | 8/1998 | Lagrange et al. |
| 6,099,592 A | 8/2000 | Vidal et al. |
| 6,099,593 A | 8/2000 | Terranova et al. |
| 6,284,003 B1 | 9/2001 | Rose et al. |
| 6,884,265 B2 | 4/2005 | Vidal et al. |
| 7,060,110 B2 | 6/2006 | Vidal et al. |
| 7,582,123 B2 | 9/2009 | Fadli et al. |
| 7,887,601 B2 * | 2/2011 | Fadli ..................... A61K 8/494 548/367.7 |

(Continued)

FOREIGN PATENT DOCUMENTS

| DE | 2359399 A1 | 6/1975 |
| DE | 3843892 A1 | 6/1990 |

(Continued)

OTHER PUBLICATIONS

STIC Search Report dated Oct. 30, 2019.*
International Search Report for counterpart Application No. PCT/EP2017/065274, dated Aug. 4, 2017.

*Primary Examiner* — Eisa B Elhilo
(74) *Attorney, Agent, or Firm* — The Marbury Law Group, PLLC

(57) ABSTRACT

The subject of the present invention is symmetric or dissymetric azomethine direct dyes comprising at least one pyrazolopyridine unit of formula (I), a composition comprising said dyes, a process for treating keratin fibers using said dyes, a process for preparing these compounds, synthesis intermediates and a kit. In which formula (I) X, $Y_1$, $Y_2$, $Z_1$, and $R_1$ to $R_5$ are as defined in the description.

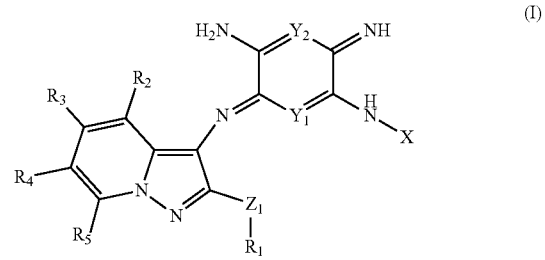

(I)

20 Claims, No Drawings

(56) References Cited

U.S. PATENT DOCUMENTS

| | | | |
|---|---|---|---|
| 7,892,294 B2 * | 2/2011 | Fadli | A61K 8/494 132/202 |
| 10,240,043 B2 * | 3/2019 | Fadli | A61Q 5/065 |
| 2002/0095732 A1 | 7/2002 | Kravtchenko et al. | |
| 2003/0106169 A1 | 6/2003 | Vidal et al. | |
| 2004/0093675 A1 | 5/2004 | Vidal et al. | |
| 2004/0107513 A1 | 6/2004 | Vidal et al. | |
| 2004/0127692 A1 | 7/2004 | David et al. | |
| 2004/0143911 A1 | 7/2004 | Vidal | |
| 2004/0168263 A1 | 9/2004 | Vidal | |
| 2004/0200009 A1 | 10/2004 | Vidal | |
| 2004/0244123 A1 | 12/2004 | Vidal et al. | |
| 2005/0039268 A1 | 2/2005 | Plos et al. | |
| 2005/0060815 A1 | 3/2005 | Kravtchenko et al. | |
| 2006/0053568 A1 | 3/2006 | Fadli | |
| 2007/0136959 A1 | 6/2007 | Fadli | |
| 2007/0143935 A1 | 6/2007 | Fadli et al. | |

FOREIGN PATENT DOCUMENTS

| | | | |
|---|---|---|---|
| DE | 4133957 A1 | 4/1993 | |
| DE | 19543988 A1 | 5/1997 | |
| EP | 0714954 A2 | 6/1996 | |
| EP | 0770375 A1 | 5/1997 | |
| EP | 1634574 A2 | 3/2006 | |
| EP | 1792606 A1 | 6/2007 | |
| EP | 1792903 A1 | 6/2007 | |
| EP | 2246038 A1 * | 11/2010 | A61Q 5/10 |
| FR | 2692572 A1 | 12/1993 | |
| FR | 2733749 A1 | 11/1996 | |
| FR | 2750048 A1 | 12/1997 | |
| FR | 2807650 A1 | 10/2001 | |
| FR | 2822693 A1 | 10/2002 | |
| FR | 2822694 A1 | 10/2002 | |
| FR | 2822696 A1 | 10/2002 | |
| FR | 2822698 A1 | 10/2002 | |
| FR | 2825625 A1 | 12/2002 | |
| FR | 2825702 A1 | 12/2002 | |
| FR | 2829926 A1 | 3/2003 | |
| FR | 2844269 A1 | 3/2004 | |
| FR | 2892924 A1 | 5/2007 | |
| FR | 2917737 A1 | 12/2008 | |
| GB | 1026978 A | 4/1966 | |
| GB | 1153196 A | 5/1969 | |
| JP | 02-019576 A | 1/1990 | |
| JP | 05-163124 A | 6/1993 | |
| WO | 94/08969 A1 | 4/1994 | |
| WO | 94/08970 A1 | 4/1994 | |
| WO | 95/01772 A1 | 1/1995 | |
| WO | 95/15144 A1 | 6/1995 | |
| WO | 96/15765 A1 | 5/1996 | |
| WO | 02/078660 A1 | 10/2002 | |
| WO | 02/100369 A2 | 12/2002 | |
| WO | 02/100834 A1 | 12/2002 | |
| WO | 2004/031173 A1 | 4/2004 | |
| WO | 2016/097198 A1 | 6/2016 | |

* cited by examiner

(DIS)SYMMETRIC AZOMETHINE-TYPE DIRECT DYE COMPRISING AT LEAST ONE PYRAZOLOPYRIDINE UNIT, PROCESS FOR DYEING KERATIN FIBERS USING THIS DYE

CROSS REFERENCE TO RELATED APPLICATIONS

This is a national stage application of PCT/EP2017/065274, filed internationally on Jun. 21, 2017, which claims priority to French Application No. 1655866, filed on Jun. 23, 2016, both of which are incorporated by reference herein in their entireties.

The subject of the present invention is symmetric or dissymmetric azomethine direct dyes comprising at least one pyrazolopyridine unit, a composition comprising said dyes, a process for treating keratin fibers using said dyes, a process for preparing these compounds, synthesis intermediates and a kit.

It is known practice to dye keratin fibers with dye compositions containing direct dyes. These compounds are colored and coloring molecules that have an affinity for the fibers. It is known practice, for example, to use direct dyes of the nitrobenzene type, anthraquinone or nitropyridine dyes, and dyes of the azo, xanthene, acridine, azine or triarylmethane type.

These dyes are usually applied to fibers optionally in the presence of an oxidizing agent if it is desired to obtain simultaneous lightening of the fibers. Once the leave-on time has elapsed, the fibers are rinsed, optionally washed and dried.

The colorings resulting from the use of direct dyes are colorings that are often chromatic but are, however, only temporary or semi-permanent since the nature of the interactions that bind the direct dyes to the keratin fiber and their desorption from the surface and/or the core of the fiber are responsible for their weak dyeing power and their poor relative persistence with respect to washing or perspiration. These direct dyes are also generally light-sensitive since the resistance of the chromophore to photochemical attack is low, leading to fading of the coloring of the hair over time. The sensitivity of these dyes to light depends on their uniform distribution or their distribution as aggregates in and/or on the keratin fiber.

To obtain the same result, it is also possible to use the uncolored reduced form of these dyes and to apply it to the keratin fibers in the presence of an oxidizing agent in order to generate the colored and coloring oxidized form. The coloring obtained may then be faded out and then reformed rapidly by changing from one form to the other.

Thus, it is known from French patent application No. 2 917 737 to use compounds of azomethine type bearing a pyrazolinone unit and the reduced forms thereof to obtain a coloring on keratin fibers that can be faded out and then reformed readily.

The aim of the present invention is to provide novel direct dyes for reversibly, gradually dyeing keratin fibers while at the same time leading to good dyeing properties.

In particular, one of the aims of the present invention is to provide direct dyes that make it possible to obtain a strong, chromatic, esthetic, sparingly selective coloring with varied shades and with good colour uptake, which shows good resistance to the various attacking factors to which the hair may be subjected such as shampoos, light or sweat and/or in the presence of oxidizing agents. Moreover the present invention provide novel direct dyes which are able to dye keratin fibers, especially natural keratin fibers such as hair, preferably white hair, in fundamental color i.e. in dark gray, blond, brown, brown chestnut, or black keratin fibers without necessarily using other hair dye than the symmetric or dissymmetric azomethine direct dyes comprising at least one pyrazolopyridine unit of the invention. Colours obtained with dyes of the invention are very esthetic and natural looking.

The applicant has thus discovered, surprisingly, that the dyes of formula (I) according to the invention make it possible to solve this (these) technical problem(s).

The dyes of the invention are azomethine compounds comprising at least one pyrazolopyridine unit, of formulae (I) below:

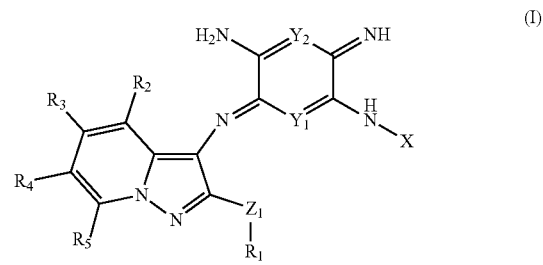

(I)

and also the leuco forms thereof, the organic or mineral acid or base salts thereof, the optical isomers, geometrical isomers and tautomers thereof, and the solvates thereof such as hydrates, in which formula (I):
$Y_1$ and $Y_2$, which may be identical or different, represent a nitrogen atom or a group C(R) with R representing a hydrogen atom or a ($C_1$-$C_6$)alkyl group;
in particular, $Y_1$ represents N and $Y_2$ represents CH or else $Y_1$ and $Y_2$ represent CH;
$Z_1$ represents an oxygen atom or a group —N($R_6$)—;
when $Z_1$ represents —N($R_6$)—, then $R_1$ and $R_6$ may form, together with the nitrogen atom to which they are attached, an optionally substituted, optionally cationic, 5- to 8-membered, saturated, unsaturated or aromatic heterocycle;
$R_1$ and $R_6$, which may be identical or different, represent:
a hydrogen atom;
a $C_1$-$C_{10}$ alkyl radical optionally interrupted with one or more non-adjacent heteroatoms, preferably oxygen, and/or optionally substituted, preferably with one or more groups chosen from i) hydroxyl, ii) optionally substituted, 5- to 8-membered, cationic or non-cationic, saturated, unsaturated or aromatic (hetero)cycle, iii) —N(R')R", iv) —N⁺R'R"R''' with R', R" and R''' each independently representing a $C_1$-$C_6$ alkyl group;
an optionally substituted, 5- to 8-membered, cationic or non-cationic, saturated, unsaturated or aromatic (hetero)cyclic radical;
in particular, $R_1$ represents a (poly)hydroxy($C_1$-$C_6$ alkyl), preferably hydroxy($C_1$-$C_6$ alkyl), group and $Z_1$ represents an oxygen atom;
$R_2$, $R_3$, $R_4$, and $R_5$, which may be identical or different, each independently represent:
a hydrogen atom;
an optionally substituted $C_1$-$C_6$ alkyl radical;
a group chosen from —$NH_2$, —N(H)$R_{10}$, —N($R_{11}$)$R_{12}$, OH and —$OR_9$, with $R_9$ and $R_{10}$ representing an optionally substituted, linear or branched $C_1$-$C_6$ alkyl, $R_{11}$ and $R_{12}$, which may be identical or different, representing an optionally substituted, linear or branched $C_1$-$C_6$ alkyl, it being possible for $R_{11}$ and $R_{12}$ to form, together with the nitrogen atom to which they are attached, a saturated, unsaturated or aromatic 5- to 8-membered heterocycle optionally containing one or more other heteroatoms or groups chosen from N, O, S, $S(O)_2$ and C(O), the heterocycle being optionally substituted;

a halide and/or $R_2$, $R_3$, $R_4$, and $R_5$ form, in pairs, with adjacent radicals, an optionally substituted, saturated or unsaturated (hetero)cycle;

X represents an optionally substituted aryl or optionally substituted heteroaryl radical;

it being understood that:

when the compounds of formula (I) are cationic, then their electro-neutrality is provided by one or more cosmetically acceptable anionic counterions, also called anions, $An^-$, which may be identical or different; and when $Y_1$ represents NH and $Y_2$ represents a CH group, then X represents a group other than a pyrazolo[1,5-a]pyridin-3-yl group which is optionally substituted.

Preferably, when $Y_1$ represents NH and $Y_2$ represents a CH group, then X represents an optionally substituted aryl group.

The colorings obtained with the dyes of formula (I) have good color uptake on the keratin fibers, have good compatibility with the oxidizing agents, and are persistent in particular against light and shampooing operations.

Furthermore, the dyes according to the invention are used for dyeing keratin fibers with varied shades, in a strong, chromatic and esthetic manner, with sparingly selective coloring, and can readily fade and/or can be easily re-dyed after fading.

More particularly, the process of the invention makes it possible to obtain strong, chromatic colorings, at various pHs, better still at neutral and basic pH, and even more preferentially at neutral pH.

Moreover the direct dyes of the invention are able to dye keratin fibers, especially natural keratin fibers such as hair, preferably white hair, in fundamental colour i.e. in gray, dark blond, brown, brown chestnut, even black keratin fibers. For instance colours obtained on keratin fibers with dyes of the invention in the L* a* b* colorimetric system (wherein L* denotes the colour intensity, a* denotes the green/red colour axis, and b*: the blue/yellow colour axis) are such as colour data a * and b * are between 0 and 5.5, especially 0 and 5.

A subject of the invention is also i) a composition comprising at least one dye of formula (I) as defined previously, ii) a process for dyeing keratin fibers by applying the composition according to the invention, iii) a process for preparing the dyes of the invention, iv) synthesis reaction intermediate compounds, and v) a kit comprising at least one dye of the invention.

Other subjects, characteristics, aspects and advantages of the invention will emerge even more clearly on reading the description and the examples that follow.

In the text hereinbelow, unless otherwise indicated, the limits of a range of values are included in that range, in particular in the expressions "between" and "ranging from . . . to . . . ".

The expression "at least one" used in the present description is equivalent to the expression "one or more".

In the context of the invention, unless otherwise mentioned, the term "alkyl radical" is intended to mean linear or branched alkyl radicals.

The saturated or unsaturated and optionally fused rings can also be optionally substituted.

The alkyl radicals are saturated, linear or branched, generally $C_1$-$C_{10}$ and particularly $C_1$-$C_6$ hydrocarbon-based radicals, preferably $C_1$-$C_4$ alkyl radicals, such as methyl, ethyl, propyl, butyl, pentyl, hexyl, isopropyl and isobutyl.

The alkenyl radicals are unsaturated, linear or branched $C_2$-$C_{10}$ hydrocarbon-based radicals, comprising at least one double bond, particularly $C_2$-$C_6$ alkenyl radicals such as ethylene, propylene, butylene, pentylene, 2-methylpropylene and decylene.

The alkynyl radicals are unsaturated, linear or branched $C_2$-$C_{10}$ hydrocarbon-based radicals, comprising at least one triple bond, particularly $C_2$-$C_6$ alkynyl radicals.

The alkoxy radicals are alkyloxy radicals with alkyl as defined above, preferably $C_1$-$C_6$ alkyl, such as methoxy, ethoxy, propoxy, isopropyloxy and butoxy.

The alkoxyalkyl radicals are preferably ($C_1$-$C_6$)alkoxy ($C_1$-$C_6$)alkyl radicals, such as methoxymethyl, ethoxymethyl, methoxyethyl and ethoxyethyl.

For the purposes of the present invention, the term "interrupted" is intended to mean that the alkyl group is interrupted in the carbon-based chain of said alkyl with one or more heteroatoms. Examples that may be mentioned include -Ak-O-Ak", -Ak-N(R)-Ak", -Ak-O-Ak'—N(R)-Ak", -Ak-N(R)-Ak'—N(R)-Ak" or -Ak-O-Ak'—O-Ak", with Ak and Ak' representing $C_1$-$C_4$ alkylene groups and Ak" representing a $C_1$-$C_4$ alkyl group.

The halogens are preferably chosen from fluorine, chlorine, bromine and iodine atoms.

The "alkylcarbonyl" radicals are alkylcarbonyl radicals with alkyl as defined previously, preferably $C_1$-$C_{10}$ alkyl, such as acetyl or propionyl.

The "alkoxycarbonyl" radicals are —O—C(O)-alkyl radicals with alkyl as defined previously, for instance acetate, propionate, citrate, tartrate, gluconate and lactate.

The "alkyl", "alkenyl", "cyclic" and "cycloalkyl" radicals, when they are substituted, are substituted with at least one substituent borne by at least one carbon atom, chosen from 1) a halogen atom, a group chosen from 2) hydroxyl; 3) oxo; 4) $C_1$-$C_2$ alkoxy; 5) $C_1$-$C_{10}$ alkoxycarbonyl; 6) $C_1$-$C_{10}$ alkylcarbonyl; 7) (poly)hydroxy($C_2$-$C_4$)alkyl; 8) (poly)hydroxy($C_2$-$C_4$)alkoxy; 9) amino; 10) quaternary ammonium —$N^+R'R''R'''$, $M^-$ for which R', R" and R''', which may be identical or different, represent a hydrogen atom or a $C_1$-$C_4$ alkyl group; and $M^-$ represents an anionic counterion, in particular a halide; 11) 5- or 6-membered heterocycloalkyl; 12) optionally cationic 5- or 6-membered heteroaryl, particularly imidazolium or pyridinium; preferentially imidazolium, optionally substituted with a $C_1$-$C_4$ alkyl radical, preferentially methyl; 13) amino substituted with one or two identical or different $C_1$-$C_6$ alkyl radicals optionally bearing at least: i) a hydroxyl group, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —$N^+R'R''R'''$, $M^-$ for which R', R" and R''', which may be identical or different, represent a hydrogen atom or a $C_1$-$C_4$ alkyl group; and $M^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 14) acylamino (—NR—C(O)R') in which the radical R is a hydrogen atom or a $C_1$-$C_4$ alkyl radical optionally bearing at least one hydroxyl group and the radical R' is a $C_1$-$C_2$ alkyl radical; 15) carbamoyl (($R)_2$N—C(O)—) in which the radicals R, which may be identical or different, represent a hydrogen atom or a $C_1$-$C_4$ alkyl radical optionally bearing at least one hydroxyl group; 16) alkylsulfonylamino (R'S($O)_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, a phenyl radical; 17) aminosulfonyl (($R)_2$N—S($O)_2$—) in which the radicals R, which may be identical or different, represent a hydrogen atom or a $C_1$-$C_4$ alkyl radical optionally bearing at least one hydroxyl group; 18) carboxyl in acid or salified form (preferably salified with an alkali metal or a substituted or unsubstituted ammonium); 19) cyano; 20) nitro; 21) nitroso; 22) phenoxy optionally substituted with one or more hydroxyl groups; 23) phenylcarbonyloxy optionally substituted with one or more hydroxyl groups; 24) phenyloxycarbonyl optionally substituted with one or more hydroxyl groups; and 25) a phenyl group optionally substituted with one or more hydroxyl groups.

The "aryl", "heterocyclic" or "heteroaryl" radicals or the aryl, heteroaryl or heterocyclic part of the radicals, when they are substituted, are substituted with at least one substituent borne by at least one carbon atom, chosen from: 1) halogen; 2) $C_1$-$C_{10}$, preferably $C_1$-$C_8$, more particularly $C_1$-$C_6$, alkyl, optionally substituted with one or more radicals chosen from the radicals i) hydroxyl, ii) $C_1$-$C_2$ alkoxy, iii) (poly)hydroxy($C_2$-$C_4$)alkoxy, iv) acylamino, v) amino substituted with two identical or different $C_1$-$C_4$ alkyl radicals, optionally bearing at least one hydroxyl group, or the two radicals being able to form, with the nitrogen atom to which they are attached, a saturated or unsaturated heterocycle comprising from 5 to 7 members, preferably 5 or 6 members, optionally comprising another heteroatom identical to or different than nitrogen, vi) halogen; vii) cationic or non-cationic heterocycle, such as $C_1$-$C_6$ alkylimidazolium $An^-$, $C_1$-$C_6$ alkylpyridinium $An^-$, $C_1$-$C_6$ alkylpiperidinium $An^-$; viii) $C_1$-$C_6$ mono/di/trialkylammonium; 3) hydroxyl; 4) $C_1$-$C_6$ alkoxy optionally substituted with one or more identical or different radicals chosen from i) hydroxyl; ii) amino, iii) $C_1$-$C_6$ mono- or dialkylamino; iv) ($C_1$-$C_6$)alkylimidazole; v) mono/di/tri($C_1$-$C_6$)alkylammonium; vi) ($C_1$-$C_6$)alkylimidazolium $An^-$; vii) ($C_1$-$C_6$)alkylpyridinium $An^-$; viii) ($C_1$-$C_6$)alkylpiperidinium $An^-$; 5) $C_1$-$C_{10}$ alkoxycarbonyl; 6) $C_1$-$C_{10}$ alkylcarbonyloxy; 7) (poly)hydroxy($C_2$-$C_4$) alkoxy; 8) amino; 9) 5- or 6-membered heterocycloalkyl; 10) optionally cationic 5- or 6-membered heteroaryl, in particular pyridinium or imidazolium, preferentially imidazolium, optionally substituted with a $C_1$-$C_4$ alkyl radical, preferentially methyl; 11) amino substituted with one or two identical or different $C_1$-$C_6$ alkyl radicals optionally bearing at least i) hydroxyl, ii) amino optionally substituted with one or two $C_1$-$C_3$ alkyl radicals, said alkyl radicals possibly forming, with the nitrogen atom to which they are attached, a saturated or unsaturated heterocycle comprising from 5 to 7 members, optionally comprising at least one other heteroatom different than or identical to nitrogen, iii) quaternary ammonium —$N^+$R'R"R'", $M^-$ for which R', R" and R'", which may be identical or different, represent a hydrogen atom or a $C_1$-$C_4$ alkyl group; and $M^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 12) quaternary ammonium —$N^+$R'R"R'", $M^-$ for which R', R", R'" and $M^-$ are as defined previously; 13) acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; 14) carbamoyl (($R)_2$N—C(O)—) in which the radicals R, which may be identical or different, represent a hydrogen atom or a $C_1$-$C_4$ alkyl radical optionally bearing at least one hydroxyl group; 15) alkylsulfonylamino (R'S($O)_2$—N(R)—) in which the radical R represents a hydrogen atom or a $C_1$-$C_4$ alkyl radical optionally bearing at least one hydroxyl group and the radical R' represents a $C_1$-$C_4$ alkyl radical or a phenyl radical; 16) aminosulfonyl (($R)_2$N—S($O)_2$—) in which the radicals R, which may be identical or different, represent a hydrogen atom or a $C_1$-$C_4$ alkyl radical optionally bearing at least one hydroxyl group; 17) carboxyl in acid or salified form (preferably salified with an alkali metal or a substituted or unsubstituted ammonium); 18) cyano; 19) nitro; 20) nitroso; 21) polyhaloalkyl, preferentially trifluoromethyl; 22) carboxyl; 23) phenylcarbonyloxy optionally substituted with one or more hydroxyl groups; 24) phenyloxycarbonyl optionally substituted with one or more hydroxyl groups; 25) phenyl optionally substituted with one or more hydroxyl or alkoxy groups; and 26) phenoxy.

The term "optionally substituted amino" radical is intended to mean an amino group which may bear one or two 1) identical or different $C_1$-$C_6$ alkyl radicals optionally bearing at least: i) a hydroxyl group, ii) an amino group optionally substituted with one or two $C_1$-$C_3$ alkyl radicals, said alkyl radicals or the two alkyl radicals form, with the nitrogen atom to which they are attached, a saturated or unsaturated, optionally substituted 5- to 7-membered heterocycle optionally comprising at least one other nitrogen or non-nitrogen heteroatom; 2) —C(O)(alkyl), the alkyl group possibly being substituted; 3) —C(O)O(alkyl), the alkyl group possibly being substituted; 4) —C(O)NH(alkyl), the alkyl group possibly being substituted; 5) —$SO_2$(alkyl), the alkyl group possibly being substituted.

The "cyclic" radicals are fused or non-fused, saturated or unsaturated, aromatic or non-aromatic, monocyclic or polycyclic, preferably monocyclic, hydrocarbon-based radicals, comprising from 4 to 15 carbon ring members, preferentially from 5 to 7 carbon atoms, optionally substituted with one or more atoms or groups as defined previously, in particular one or more alkyl, alkoxy, carboxyl, hydroxyl, amine or oxo groups.

The "aryl" radicals are fused or non-fused, monocyclic or polycyclic carbon-based radicals, preferentially comprising from 6 to 20 carbon atoms, and of which at least one ring is aromatic; preferentially chosen from phenyl, biphenyl, naphthyl, indenyl, anthracenyl and tetrahydronaphthyl radicals; more preferentially, the aryl radicals of the invention are phenyl radicals.

The "heterocyclic" radicals are fused or non-fused, saturated or unsaturated, aromatic or non-aromatic, monocyclic or polycyclic, optionally cationic, 4- to 30-membered, preferentially 5- to 15-membered radicals, in at least one ring at least one ring member is a heteroatom, chosen in particular from O, N and S, preferably comprising from 1 to 6 heteroatoms, in particular 0 or N, optionally substituted with one or more atoms or groups as defined previously, in particular one or more alkyl, alkoxy, carboxyl, hydroxyl, amine or oxo groups.

When the heterocycle is cationic, then it bears a cationic charge inside the ring (endocyclic) or outside the ring (exocyclic), i.e. the heterocycle is substituted with a cationic group.

The "heteroaryl" radicals are fused or non-fused, preferentially 5- to 22-membered monocyclic or polycyclic radicals, comprising from 1 to 6 heteroatoms chosen from nitrogen, oxygen and sulfur atoms, and at least one ring of which is aromatic; preferentially, the heteroaryl radicals are chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrazolopyridine, pyrrolyl, quinolyl, tetrazolyl, thiadiazolyl, thiazolyl, thiazolopyridinyl, thiazoylimidazolyl, thiopyrylyl, triazolyl, xanthylyl and the ammonium salts thereof.

Among the heterocyclic radicals that may be used in the invention, mention may be made particularly of furyl, pyranyl, pyrrolyl, piperazinyl, piperidinyl, morpholinyl, imidazolyl, pyrazolyl, pyridyl and thienyl groups. Preferably, the heterocyclic groups are fused heteroaryl groups such as benzofuranyl, chromenyl, xanthenyl, indolyl, isoindolyl, quinolyl, isoquinolyl, chromanyl, isochromanyl, indolinyl, isoindolinyl, coumarinyl, isocoumarinyl or pyrazolopyridinyl groups, these groups possibly being substituted, in particular with one or more non-adjacent hydroxyl groups.

The "heterocycloalkyl" radicals are saturated heterocyclic radicals as defined previously, such as tetrahydrofuranyl, tetrahydropyranyl, piperazinyl, piperidinyl or morpholinyl.

The cycloalkyl radicals are cyclic radicals as defined previously, preferably saturated $C_4$-$C_8$ monocyclic radicals, such as cyclobutyl, cyclopentyl or cyclohexyl. The cycloalkyl radicals may be substituted, in particular with alkyl, alkoxy, carboxylic acid, hydroxyl, amine and ketone groups.

The nitrogenous heterocycle(s) formed by $R_1$ and $R_6$, and/or $R'_6$ and $R'_7$ may contain one or more other heteroatoms, in particular a heteroatom chosen from N, O and S, one or more groups such as —S(O)—, —S(O)$_2$— and —C(O)—, and combinations thereof, and more particularly O or N. They may moreover be optionally substituted, in particular as described above.

The term "anionic counterion" is intended to mean an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methylsulfonate or mesylate and ethylsulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O—)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or SO$_4^{2-}$ and monosulfate HSO$_4^-$.

The anionic counterion, derived from the organic or mineral acid salt, ensures the electro-neutrality of the molecule; thus, it is understood that when the anion comprises several anionic charges, then the same anion may serve for the electro-neutrality of several cationic groups in the same molecule or else may serve for the electro-neutrality of several molecules; for example, a dye of formula (I) which contains two cationic charges may contain either two "singly charged" anionic counterions or a "doubly charged" anionic counterion such as (O=)$_2$S(O$^-$)$_2$ or O=P(O$^-$)$_2$—OH.

A subject of the invention is thus a compound chosen from dyes of azomethine type comprising a pyrazolopyridine unit of formula (I) and the leuco forms thereof corresponding to the reduced form of (I) of formula below,

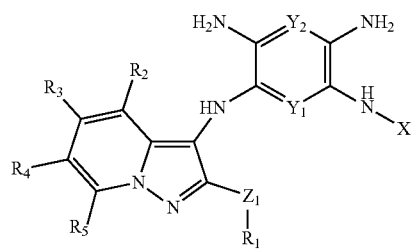

Leuco form of (I)

and also the optical isomers, geometrical isomers and tautomers thereof, the acid or base addition salts thereof, and the solvates thereof such as hydrates.

According to one particular embodiment of the invention, the compounds (I) are such that $Y_1$ represents N and $Y_2$ represents a group C(R) with R as defined previously and in particular CH.

According to one preferred mode of the invention, $Y_1$ and $Y_2$ represent a group C(R) with R as defined previously and in particular CH.

According to one particular embodiment of the invention, the compounds of formula (I) are such that X represents a group chosen from those of formula (II) or of formula (III):

(II)

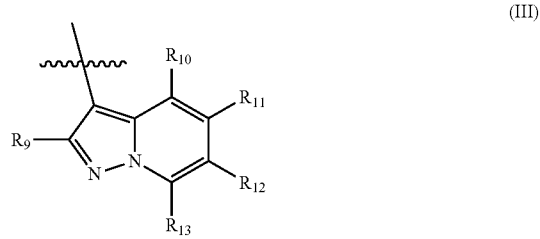

(III)

in which formulae (II) and (III):

〰〰 corresponds to the point of anchorage of the group (II) or (III) to the rest of the molecule;

Ar represents an aryl group optionally substituted, in particular substituted, with one or more radicals $R_8$, which may be identical or different, $R_8$ representing an atom or group chosen from:

halogen;

—OR'$_{14}$;

—NR$_{14}$R$_{15}$;

$C_1$-$C_6$ alkyl optionally substituted with one or more atoms or groups, which may be identical or different, chosen from i) hydroxyls, ii) amino, iii) ($C_1$-$C_6$)

alkylamino, iv) di($C_1$-$C_6$)alkylamino, v) halogen, vi) ($C_1$-$C_6$)alkylimidazolyl, v) tri($C_1$-$C_6$)alkylammonium $An^-$, vi) ($C_1$-$C_6$)alkylimidazolium $An^-$, vii) ($C_1$-$C_6$)alkylpyridinium $An^-$, viii) ($C_1$-$C_6$)alkylpiperidinium $An^-$;

carboxyl (—C(O)—OH);

carboxamide (—C(O)—$NR^aR^b$) with $R^a$ and $R^b$, which may be identical or different, representing a hydrogen atom or a ($C_1$-$C_4$)alkyl group, preferably a hydrogen atom;

preferentially, $R_8$ is in position 4, more preferentially $R_8$ represents a radical —$NR_{14}R_{15}$; and $R_9$ represents:
  a radical —$OR'_6$; or
  a radical —$NR'_6R'_7$; preferably $R_9$ represents a radical —$OR'_6$;

when $R_9$ represents —$NR'_6R'_7$ then $R'_6$ and $R'_7$ can form, together with the nitrogen atom to which they are attached, an optionally substituted, optionally cationic, 5- to 8-membered, saturated, unsaturated or aromatic heterocycle;

$R'_6$ and $R'_7$, which may be identical or different, represent:
  a hydrogen atom;
  a $C_1$-$C_{10}$ alkyl radical optionally interrupted with one or more non-adjacent heteroatoms, preferably oxygen, and/or optionally substituted, preferably with one or more groups chosen from i) hydroxyl, ii) optionally substituted, 5- to 8-membered, cationic or non-cationic, saturated, unsaturated or aromatic (hetero)cycle, iii) —N(R')R", iv) —$N^+R'R"R'"$ with R', R" and R'" each independently representing a $C_1$-$C_6$ alkyl group;
  an optionally substituted, 5- to 8-membered, cationic or non-cationic, saturated, unsaturated or aromatic (hetero)cyclic radical;

in particular, $R_9$ represents —$OR'_6$ with $R'_6$ representing a (poly)hydroxy($C_1$-$C_6$ alkyl), preferably hydroxy($C_1$-$C_6$ alkyl), group;

$R_{10}$, $R_{11}$, $R_{12}$ and $R_{13}$, which may be identical or different, represent:
a hydrogen atom;
an optionally substituted $C_1$-$C_4$ alkyl radical;
a group chosen from —$NH_2$, —N(H)$R_{16}$, —N($R_{17}$)$R_{18}$, OH and —$OR_{19}$, with $R_{16}$ and $R_{19}$ independently representing an optionally substituted, linear or branched $C_1$-$C_6$ alkyl, $R_{17}$ and $R_{18}$, which may be identical or different, representing an optionally substituted, linear or branched $C_1$-$C_6$ alkyl, it being possible for $R_{17}$ and $R_{18}$ to form, together with the nitrogen atom to which they are attached, a saturated, unsaturated or aromatic 5- to 8-membered heterocycle optionally containing one or more other heteroatoms or groups chosen from N, O, S, S(O)$_2$ and C(O), the heterocycle being optionally substituted; and/or $R_{10}$, $R_{11}$, $R_{12}$, and $R_{13}$ form, in pairs, with adjacent radicals, an optionally substituted, saturated or unsaturated (hetero)cycle; preferably, $R_{10}$, $R_{11}$, $R_{12}$ and $R_{13}$ represent a hydrogen atom;

$R_{14}$ and $R_{15}$, which may be identical or different, represent an atom or group chosen from:
  a hydrogen atom;
  a linear or branched $C_1$-$C_6$ alkyl radical which may be substituted with one or more radicals, which may be identical or different, chosen from hydroxyls, amino, ($C_1$-$C_6$)alkylamino or di($C_1$-$C_6$)alkylamino, ($C_1$-$C_6$) alkylimidazole, mono/di/tri($C_1$-$C_6$)alkylammonium, $An^-$, ($C_1$-$C_6$)alkylimidazolium $An^-$, ($C_1$-$C_6$)alkylpyridinium $An^-$; ($C_1$-$C_6$)alkylpiperidinium, $An^-$; or else $R_{14}$ and $R_{15}$ form, together with the nitrogen to which they are attached, a cationic or non-cationic 4- to 7-membered heterocycle which may also contain one or more heteroatoms such as nitrogen, oxygen and/or sulfur, said heterocycle possibly being substituted with one or more radicals, which may be identical or different, chosen from hydroxyl, amino, (di)($C_1$-$C_6$)alkylamino, $C_1$-$C_6$ alkoxy, mono/di/tri($C_1$-$C_6$)alkylammonium, $An^-$; ($C_1$-$C_6$)alkylimidazolium, $An^-$; ($C_1$-$C_6$)alkylpyridinium, $An^-$; or $C_1$-$C_6$ alkyl;

$R'_{14}$ represents an atom or group chosen from:
  hydrogen;
  linear or branched $C_1$-$C_6$ alkyl which may be substituted with one or more radicals, which may be identical or different, chosen from hydroxyl, amino, ($C_1$-$C_6$)alkylamino or di($C_1$-$C_6$)alkylamino, ($C_1$-$C_6$) alkylimidazole, mono/di/tri($C_1$-$C_6$)alkylammonium $An^-$, ($C_1$-$C_6$)alkylimidazolium $An^-$, ($C_1$-$C_6$)alkylpyridinium $An^-$, ($C_1$-$C_6$)alkylpiperidinium $An^-$;

it being understood that:
when the compounds of formula (I) are cationic, then their electro-neutrality is provided by one or more anionic counterions $An^-$; and
when $Y_1$ represents NH and $Y_2$ represents a CH group, then X represents a radical (II).

According to one particular embodiment of the invention, the compounds of formula (I) are such that X represents a group chosen from those of formula (III) with:

$R_9$ representing:
  a radical —$NR'_6R'_7$ with $R'_6$ and $R'_7$, which form, together with the nitrogen atom to which they are attached, a saturated, optionally substituted, optionally cationic, preferably catonic, 5- to 8-membered heterocycle, or else $R'_6$ and $R'_7$, which may be identical or different, represent:
  a hydrogen atom;
  a $C_1$-$C_{10}$ alkyl radical optionally substituted, preferably with one or more groups chosen from i) hydroxyl, ii) optionally substituted, 5- to 8-membered, cationic or non-cationic, saturated, unsaturated or aromatic (hetero)cycle, iii) —N(R')R", iv) —$N^+R'R"R'"$ with R', R" and R'" each independently representing a $C_1$-$C_6$ alkyl group;
or
  a radical —$OR'_6$ with $R'_6$ representing a $C_1$-$C_{10}$ alkyl radical optionally interrupted with one or more non-adjacent heteroatoms, preferably oxygen, and/or optionally substituted, preferably with one or more groups chosen from i) hydroxyl, ii) optionally substituted, 5- to 8-membered, cationic or non-cationic, saturated, unsaturated or aromatic (hetero)cycle, iii) —N(R')R", iv) —$N^+R'R"R'"$ with R', R" and R'" each independently representing a $C_1$-$C_6$ alkyl group;

in particular, $R_9$ represents —$OR'_6$ with $R'_6$ representing a (poly)hydroxy($C_1$-$C_6$ alkyl), preferably hydroxy($C_1$-$C_6$ alkyl), group;

$R_{10}$, $R_{11}$, $R_{12}$ and $R_{13}$, which may be identical or different, represent an atom or group chosen from:
  hydrogen;
  halogen;
  linear or branched $C_1$-$C_6$ alkyl which may be substituted with one or more radicals, which may be identical or different, chosen from hydroxyls, amino, ($C_1$-$C_6$)alkylamino or di($C_1$-$C_6$)alkylamino;

linear or branched $C_1$-$C_6$ alkoxy which may be substituted with one or more radicals, which may be identical or different, chosen from hydroxyls, amino, ($C_1$-$C_6$)alkylamino or di($C_1$-$C_6$)alkylamino;

preferably, $R_{10}$, $R_{11}$, $R_{12}$, and $R_{13}$ represent a hydrogen atom.

According to one embodiment of the invention, the dyes are of formula (I) in which X represents an aryl group of formula (II) with:

Ar represents a substituted aryl group, of which at least one of the substituents $R_8$ represents a radical —$OR'_{14}$ and/or —$NR_{14}R_{15}$, more preferentially $R_8$ represents a radical —$NR_{14}R_{15}$, particularly —$OR'_{14}$ and —$NR_{14}R_{15}$ are in position 4 of said aryl, more particularly the aryl group is a phenyl substituted in position 4 with —$NR_{14}R_{15}$;

$R_{14}$ and $R_{15}$, which may be identical or different, represent an atom or group chosen from:
- a hydrogen atom;
- a linear or branched $C_1$-$C_6$ alkyl radical which may be substituted with one or more radicals, which may be identical or different, chosen from hydroxyls, amino, ($C_1$-$C_6$)alkylamino or di($C_1$-$C_6$)alkylamino, ($C_1$-$C_6$)alkylimidazole, mono/di/tri($C_1$-$C_6$)alkylammonium, $An^-$, ($C_1$-$C_6$)alkylimidazolium $An^-$, ($C_1$-$C_6$)alkylpyridinium $An^-$; ($C_1$-$C_6$)alkylpiperidinium, $An^-$; or else
- $R_{14}$ and $R_{15}$ form, together with the nitrogen to which they are attached, a cationic or non-cationic 4- to 7-membered heterocycle which may also contain one or more heteroatoms such as nitrogen, oxygen and/or sulfur, said heterocycle possibly being substituted with one or more radicals, which may be identical or different, chosen from hydroxyl, amino, (di)($C_1$-$C_6$)alkylamino, $C_1$-$C_6$ alkoxy, mono/di/tri($C_1$-$C_6$)alkylammonium, $An^-$; ($C_1$-$C_6$)alkylimidazolium, $An^-$; ($C_1$-$C_6$)alkylpyridinium, $An^-$; or $C_1$-$C_6$ alkyl;

$R'_{14}$ represents an atom or group chosen from:
- hydrogen;
- linear or branched $C_1$-$C_6$ alkyl which may be substituted with one or more radicals, which may be identical or different, chosen from hydroxyl, amino, ($C_1$-$C_6$)alkylamino or di($C_1$-$C_6$)alkylamino, ($C_1$-$C_6$)alkylimidazole, mono/di/tri($C_1$-$C_6$)alkylammonium $An^-$, ($C_1$-$C_6$)alkylimidazolium $An^-$, ($C_1$-$C_6$)alkylpyridinium $An^-$, ($C_1$-$C_6$)alkylpiperidinium $An^-$.

According to one preferred embodiment of the invention, the compounds of formula (I) are such that:

$Z_1$ represents an oxygen atom or a group —N($R_6$)—, preferably $Z_1$ represents an oxygen atom;

$R_2$, $R_3$, $R_4$ and $R_5$, which may be identical or different, represent an atom or group chosen from:
- hydrogen;
- halogen such as fluorine or chlorine;
- linear or branched $C_1$-$C_6$ alkyl which may be substituted with one or more radicals, which may be identical or different, chosen from hydroxyls, amino, mono($C_1$-$C_6$)alkylamino or di($C_1$-$C_6$)alkylamino; and
- linear or branched $C_1$-$C_6$ alkoxy which may be substituted with one or more radicals, which may be identical or different, chosen from hydroxyls, amino, mono($C_1$-$C_6$)alkylamino or di($C_1$-$C_6$)alkylamino;

preferably, $R_2$, $R_3$, $R_4$ and $R_5$ represent a hydrogen atom;

$R_1$ and $R_6$, and/or $R'_6$ and $R'_7$, which may be identical or different, represent an atom or group chosen from:
- a hydrogen atom;
- a linear or branched $C_1$-$C_6$ alkyl radical which may be substituted with one or more radicals, which may be identical or different, chosen from a) hydroxyls; b) amino; c) ($C_1$-$C_6$)alkylamino; d) di($C_1$-$C_6$)alkylamino; e) ($C_1$-$C_6$)alkylimidazolyl; f) mono/di/tri ($C_1$-$C_6$)alkylammonium, $An^-$; g) ($C_1$-$C_6$)alkylimidazolium, $An^-$; h) ($C_1$-$C_6$)alkylpyridinium, $An^-$; i) ($C_1$-$C_6$)alkylpiperidinium, $An^-$; j) (di)($C_1$-$C_6$)alkylpiperazinium, $An^-$; k) morpholino and l) ($C_1$-$C_6$)alkylmorpholinium;

in particular, $R_1$ and $R_6$, and/or $R'_6$ and $R'_7$, which may be identical or different, represent a hydrogen atom and/or a $C_1$-$C_4$ alkyl radical optionally substituted with one or more hydroxyl groups such as 2-hydroxyethyl;

or else $R_1$ and $R_6$, and/or $R'_6$ and $R'_7$ form, together with the nitrogen atom to which they are attached, a cationic or non-cationic, monocyclic, 4- to 7-membered heterocycle which may also contain one or more heteroatoms in particular chosen from nitrogen, oxygen and sulfur, said heterocycle possibly being substituted with one or more radicals, which may be identical or different, chosen from the radicals a) hydroxyls; b) amino; c) ($C_1$-$C_6$)alkylamino; d) di($C_1$-$C_6$)alkylamino; e) ($C_1$-$C_6$)alkoxy; f) mono/di/tri($C_1$-$C_6$)alkylammonium, $An^-$; g) ($C_1$-$C_6$)alkylimidazolium, $An^-$; h) ($C_1$-$C_6$)alkylpyridinium $An^-$; i) $C_1$-$C_6$ alkyl; j) (di)($C_1$-$C_6$)alkylpiperazinium, $An^-$; k) morpholino and l) ($C_1$-$C_6$)alkylmorpholinium; in particular, said heterocycle is cationic comprising 5 or 6 members, and saturated, and can also comprise a heteroatom such as oxygen or nitrogen, preferably nitrogen, substituted with one or more ($C_1$-$C_4$)alkyls such as (di)($C_1$-$C_4$)alkylpiperazinium, $An^-$(N,N-dimethylpiperazinium);

preferably, $R_1$ and $R_6$, and/or $R'_6$ and $R'_7$ independently represent a 2-hydroxyethyl radical or together an N,N-dimethylpiperazinium radical;

$R_1$ and $R'_6$, which may be identical or different, represent an atom or group chosen from:
- hydrogen;
- linear or branched $C_1$-$C_6$ alkyl which may be substituted with one or more radicals, which may be identical or different, chosen from a) hydroxyls; b) amino; c) ($C_1$-$C_6$)alkylamino; d) di($C_1$-$C_6$)alkylamino; e) ($C_1$-$C_6$)alkylimidazole; f) mono/di/tri($C_1$-$C_6$)alkylammonium, $An^-$; g) ($C_1$-$C_6$)alkylimidazolium, $An^-$; h) ($C_1$-$C_6$)alkylpyridinium, $An^-$; i) ($C_1$-$C_6$)alkylpiperidinium, $An^-$; preferably a $C_1$-$C_6$ alkyl group optionally substituted with one or more hydroxyl groups, such as hydroxyethyl;

X represents a radical of formula (II') or of formula (III):

(II')

$R_8$ ($R_8'$)$_n$

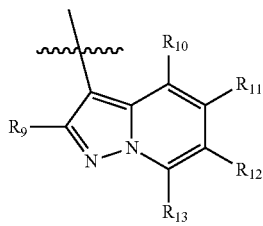

(III)

in which formulae (II') and (III):

~~~~ corresponds to the point of anchorage of the group (II) or (III) to the rest of the molecule;

n represents an integer between 0 and 4; preferably n is 0, 1 or 2 and more preferentially n is 0; when n is greater than or equal to 2, then the radicals $R'_8$ may be identical or different;

$R'_8$ represents an atom or group chosen from:
1) halogen such as fluorine or chlorine; 2) $C_1$-$C_6$, preferably $C_1$-$C_4$, alkyl, optionally substituted with one or more radicals chosen from the radicals i) hydroxyl, ii) $C_1$-$C_2$ alkoxy, iii) (poly)hydroxy($C_2$-$C_4$)alkoxy, iv) acylamino, v) amino substituted with one or two identical or different $C_1$-$C_4$ alkyl radicals, optionally bearing at least one hydroxyl group, or the two radicals being able to form, with the nitrogen atom to which they are attached, a saturated or unsaturated heterocycle comprising from 5 to 7 members, preferably 5 or 6 members, optionally comprising another heteroatom identical to or different than nitrogen, vi) halogen; vii) cationic or non-cationic heterocycle, such as $C_1$-$C_6$ alkylimidazolium $An^-$, $C_1$-$C_6$ alkylpyridinium $An^-$, $C_1$-$C_6$ alkylpiperidinium $An^-$; viii) $C_1$-$C_6$ mono/di/trialkylammonium; 3) hydroxyl; 4) $C_1$-$C_6$ alkoxy optionally substituted with one or more identical or different radicals chosen from i) hydroxyl; ii) amino, iii) $C_1$-$C_6$ mono- or dialkylamino; iv) ($C_1$-$C_6$)alkylimidazole; v) mono/di/tri($C_1$-$C_6$)alkylammonium; vi) ($C_1$-$C_6$)alkylimidazolium $An^-$; vii) ($C_1$-$C_6$)alkylpyridinium $An^-$; viii) ($C_1$-$C_6$)alkylpiperidinium $An^-$; 5) $C_1$-$C_6$ alkoxycarbonyl; 6) $C_1$-$C_6$ alkylcarbonyloxy; 7) (poly)hydroxy($C_2$-$C_4$)alkoxy; 8) amino; 9) 5- or 6-membered heterocycloalkyl; 10) optionally cationic 5- or 6-membered heteroaryl, preferentially imidazolium, optionally substituted with a $C_1$-$C_4$ alkyl radical, preferentially methyl; 11) amino substituted with one or two identical or different $C_1$-$C_6$ alkyl radicals optionally bearing at least i) hydroxyl, ii) amino optionally substituted with one or two $C_1$-$C_3$ alkyl radicals, said alkyl radicals possibly forming, with the nitrogen atom to which they are attached, a saturated or unsaturated heterocycle comprising from 5 to 7 members, optionally comprising at least one other heteroatom different than or identical to nitrogen, iii) quaternary ammonium —N+R'R"R"', M− for which R', R" and R"', which may be identical or different, represent a hydrogen atom or a $C_1$-$C_4$ alkyl group; and M− represents an anionic counterion, in particular a halide, iv) optionally cationic 5- or 6-membered heteroaryl, preferentially imidazolium, optionally substituted with a $C_1$-$C_4$ alkyl radical, preferentially methyl; 12) quaternary ammonium —N+R'R"R"', M− for which R', R", R"' and M− are as defined previously; 13) acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; 14) carbamoyl ((R)$_2$N—C(O)—) in which the radicals R, which may be identical or different, represent a hydrogen atom or a $C_1$-$C_4$ alkyl radical optionally bearing at least one hydroxyl group; 15) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical or a phenyl radical; 16) aminosulfonyl ((R)$_2$N—S(O)$_2$—) in which the radicals R, which may be identical or different, represent a hydrogen atom or a $C_1$-$C_4$ alkyl radical optionally bearing at least one hydroxyl group; 17) carboxyl in acid or salified form (preferably salified with an alkali metal or a substituted or unsubstituted ammonium); 18) cyano; 19) nitro; 20) polyhaloalkyl, preferentially trifluoromethyl; 21) carboxyl; 22) phenylcarbonyloxy optionally substituted with one or more hydroxyl groups; 23) phenyloxycarbonyl optionally substituted with one or more hydroxyl groups; 24) phenyl optionally substituted with one or more hydroxyl or alkoxy groups; and 25) phenoxy;

or else, when n is greater than or equal to 2, two contiguous radicals $R'_8$ form, together with the carbon atoms which bear them, an optionally substituted (hetero)cycle;

$R_8$ represents an atom or group chosen from:
hydrogen;
halogen;
—$OR'_{14}$;
—$NR_{14}R_{15}$;
$C_1$-$C_6$ alkyl optionally substituted with one or more radicals, which may be identical or different, chosen from hydroxyls, amino, $C_1$-$C_6$ monoalkylamino or dialkylamino, halogen, $C_1$-$C_6$ alkylimidazole, $C_1$-$C_6$ trialkylammonium $An^-$, $C_1$-$C_6$ alkylimidazolium $An^-$, $C_1$-$C_6$ alkylpyridinium $An^-$, $C_1$-$C_6$alkylpiperidinium $An^-$;
carboxyl (—$CO_2H$);
carboxamide (—$CO_2NH_2$);

preferably, $R_9$ represents a radical —$NR_{14}R_{15}$;
$R_9$ represents
a radical —$OR'_6$; or
a radical —$NR'_6R'_7$; preferably $R_9$ represents a radical —$OR'_6$;

$R_{10}$, $R_{11}$, $R_{12}$ and $R_{13}$, which may be identical or different, represent an atom or group chosen from:
hydrogen;
halogen;
linear or branched $C_1$-$C_6$ alkyl which may be substituted with one or more radicals, which may be identical or different, chosen from hydroxyls, amino, ($C_1$-$C_6$)alkylamino or di($C_1$-$C_6$)alkylamino;
linear or branched $C_1$-$C_6$ alkoxy which may be substituted with one or more radicals, which may be identical or different, chosen from hydroxyls, amino, ($C_1$-$C_6$)alkylamino or di($C_1$-$C_6$)alkylamino;

$R_{14}$ and $R_{15}$, which may be identical or different, represent an atom or group chosen from:
a hydrogen atom;
a linear or branched $C_1$-$C_6$ alkyl radical optionally substituted in particular with one or more radicals, which may be identical or different, chosen from hydroxyls, amino, $(C_1-C_6)$alkylamino or di$(C_1-C_6)$alkylamino, $(C_1-C_6)$alkylimidazole, mono/di/tri$(C_1-C_6)$alkylammonium, An⁻, $(C_1-C_6)$alkylimidazolium An⁻, $(C_1-C_6)$alkylpyridinium An⁻; $(C_1-C_6)$alkylpiperidinium, An⁻; or else $R_{14}$ and $R_{15}$ form, together with the nitrogen to which they are attached, a cationic or non-cationic 4- to 7-membered heterocycle which may also contain one or more heteroatoms such as nitrogen, oxygen and/or sulfur, said heterocycle possibly being substituted with one or more radicals, which may be identical or different, chosen from hydroxyl, amino, (di)$(C_1-C_6)$alkylamino, $C_1-C_6$ alkoxy, mono/di/tri $(C_1-C_6)$alkylammonium, An⁻; $(C_1-C_6)$alkylimidazolium, An⁻; $(C_1-C_6)$alkylpyridinium, An⁻; or $C_1-C_6$ alkyl;

$R'_{14}$ represents an atom or group chosen from:
hydrogen;
linear or branched $C_1-C_6$ alkyl optionally substituted in particular with one or more radicals, which may be identical or different, chosen from hydroxyl, amino, $(C_1-C_6)$alkylamino or di$(C_1-C_6)$alkylamino, $(C_1-C_6)$alkylimidazole, mono/di/tri$(C_1-C_6)$alkylammonium An⁻, $(C_1-C_6)$alkylimidazolium An⁻, $(C_1-C_6)$alkylpyridinium An⁻, $(C_1-C_6)$alkylpiperidinium An⁻;

it being understood that:
when the compounds of formula (I) are cationic, then their electro-neutrality is provided by one or more cosmetically acceptable anionic counterion anions, An⁻, which may be identical or different; and
when $Y_1$ represents NH and $Y_2$ represents a CH group, then X represents a radical (II) or (II').

According to one preferred embodiment, X represents a radical of formula (II) or (II') as defined previously.

More particularly, X represents a radical (II) or (II') with $R_9$ representing a radical —$NR_{14}R_{15}$. Preferentially, $R_{14}$ represents an atom or group chosen from i) hydrogen and ii) $(C_1-C_4)$alkyl optionally substituted with one or more hydroxyl groups, and $R_{15}$ represents an atom or group chosen from i) hydrogen and ii) $(C_1-C_6)$alkyl optionally substituted with one or more hydroxyl groups, or heterocycles, preferably cationic heterocycles, such as $(C_1-C_4)$ alkylimidazolinium, An⁻.

According to another preferred embodiment, X represents a radical (III) as defined previously.

In formula (I), when X represents a radical (III) and $R_9$ represents a group —$NR'_6R'_7$, $R'_6$, and/or $R'_7$ represent(s) a substituted alkyl radical, then the substituents are in particular chosen from halogen atoms, —OH, —$OR'_9$, —$NH_2$, —$N(H)R'_{10}$ or —$N(R'_{11})R'_{12}$ radicals, saturated or unsaturated cyclic radicals optionally containing a heteroatom chosen from N, S and O, the ring itself possibly being substituted, in which $R'_9$, $R'_{10}$, $R'_{11}$ and $R'_{12}$, which may be identical or different, represent a saturated linear or branched $C_1-C_6$ and preferably $C_1-C_4$ alkyl radical, such as methyl or ethyl. Preferably, mention may be made of —OH, —$OR'_9$, —$NH_2$, —$N(H)R'_{10}$ or —$N(R'_{11})R'_{12}$ radicals and cyclic radicals such as imidazole, piperazine, pyrrolidine, pyridine, piperidine, morpholine and pyrimidine.

According to one particular embodiment of the invention, the compounds of formula (I) above are such that $Z_1$ represents a radical —$N(R_6)$— and X represents a radical (III) with $R_9$ representing a group —$N(R'_6)$—R', in which $R_1$ and $R_6$ and/or $R'_6$ and $R'_7$ form, together with the nitrogen atom which bears them, a cationic or non-cationic heterocycle chosen from piperazinyl, piperazinium, imidazolyl, pyrrolidinyl, pyridinyl, morpholinyl, morpholinium, piperidinyl, piperidinium, preferentially piperazinyl, piperazinium optionally substituted in particular with one or more $C_1-C_4$ alkyl groups such as methyl; preferably piperazinium optionally substituted in particular with a $C_1-C_4$ alkyl group such as methyl.

According to another preferred embodiment of the invention, $Z_1$ represents an oxygen atom or a radical NH and X represents a radical (III) and $R_9$ represents a group —O—$R'_6$ or —N(H)—$R'_6$ with $R'_6$ as defined previously.

According to another preferred embodiment of the invention, $Z_1$ represents a radical —$N(R_6)$— and X represents a radical (II) or (II') as defined previously with $R_1$ and $R_6$ representing a cationic or non-cationic heterocycle, such as piperazinyl, piperazinium, imidazolyl, pyrrolidinyl, pyridinyl, morpholinyl, morpholinium, piperidinyl, piperidinium, preferentially piperazinyl, piperazinium optionally substituted in particular with one or more $C_1-C_4$ alkyl groups such as methyl; piperazinium optionally substituted in particular with a $C_1-C_4$ alkyl group such as methyl.

According to the invention, the radicals $R_1$, $R_6$ and/or $R'_6$ are particularly chosen from the following groups: i) $C_1-C_6$ alkyl; ii) $C_1-C_{10}$ alkyl substituted with one or more hydroxyl groups; iii) $C_1-C_6$ alkyl substituted with one or more amino or (di)$(C_1-C_4)$alkylamino groups such as dimethylamino; iv) $C_1-C_6$ alkyl substituted with a nitrogenous heterocycle, for example piperazinyl, imidazolyl, pyrrolidinyl, morpholinyl or piperidinyl; v) —$[(CH_2)_m$—O$]_p$-L-Y with p=1, 2 or 3, preferably 1 or 2, m=1, 2 or 3, preferably 2, L denoting a linear or branched, saturated $C_1-C_6$ divalent hydrocarbon-based group, and Y denoting a hydroxyl group or a hydrogen atom.

The radicals $R_1$, $R_6$ and/or $R'_6$ is (are) particularly chosen from a hydrogen atom, a $C_1-C_6$ alkyl radical and a $C_1-C_6$ alkyl radical substituted with one or more hydroxyl groups.

According to one particular embodiment of the invention, the radicals $R_1$, $R_6$ and/or $R'_6$ represent a $C_1-C_6$ alkyl group such as a methyl, ethyl, n-propyl, isopropyl or tert-butyl radical; a $C_1-C_6$ alkyl radical substituted with a hydroxyl group such as a hydroxyethyl or hydroxypropyl radical; a $C_1-C_6$ alkyl radical substituted with a di$(C_1-C_4)$alkylamino such as a dimethylaminoethyl or dimethylaminopropyl radical; a $C_1-C_6$ alkyl radical substituted with a nitrogenous heterocycle chosen from imidazolyl, pyrrolidinyl, piperidinyl, morpholidinyl and piperazinyl, these heterocycles possibly being substituted or unsubstituted; or a radical —$[(CH_2)_m$—O$]_p$-L-Y with m=2, p=1 or 2, L denoting an ethylene or isopropylene radical, and Y denoting a hydroxyl radical or a hydrogen atom.

According to the particular embodiment in which $Z_1$ represents —$NR_6$ and X represents (III) with $R_9$ denoting a radical and —$NR'_6$ with $R_1$ and $R_6$ and $R'_6$ and $R'_7$ together forming a heterocycle with the nitrogen atom to which they are attached, the heterocycle is preferentially chosen from imidazolyl, piperazino, pyrrolidino, piperidino and morpholino, these heterocycles possibly being unsubstituted or substituted, in particular with one or more $C_1-C_4$ alkyl or hydroxyl radicals.

According to a particular embodiment, the azomethine dyes bearing two pyrazolopyridine units are chosen from the symmetrical compounds of formulae (I') below, and also the leuco forms, optical isomers, geometrical isomers and tautomers thereof, the acid or base addition salts thereof and the solvates thereof such as hydrates:

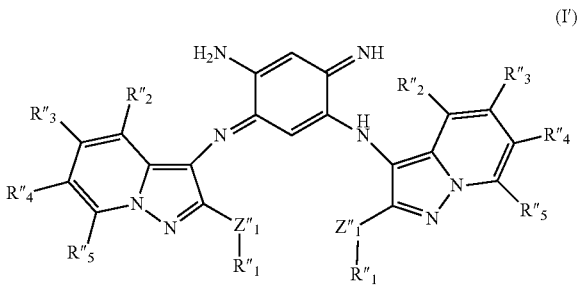

(I')

in which formula (I'):
- $Z''_1$ is chosen from an oxygen atom or a group $-N(R''_6)-$;
- when $Z''_1$ represents $-N(R''_6)-$ then $R''_1$ and $R''_6$ may form, together with the nitrogen atom to which they are attached, a cationic or non-cationic, saturated, optionally unsaturated, heterocycle comprising 5 or 6 members, optionally substituted preferably with one or more $(C_1-C_4)$alkyl groups such as piperazinium, piperidinium or morpholinium optionally substituted with a $(C_1-C_4)$alkyl group;
- $R''_1$ represents a $C_1-C_6$ alkyl radical, optionally interrupted with one or more non-adjacent oxygen atoms, and/or optionally substituted with:
  - a hydroxyl radical,
  - a di$(C_1-C_4)$alkylamino radical,
  - a heterocycle optionally substituted with one or more $C_1-C_4$ alkyl and/or hydroxyl radicals and chosen from pyrrolidine, piperidine, morpholine, piperazine and imidazole;
- $R''_6$ represents:
  - a hydrogen atom,
  - a $C_1-C_{10}$ alkyl radical optionally substituted with a hydroxyl radical;
- $R''_2$, $R''_3$, $R''_4$ and $R''_5$ each independently represent:
  - a hydrogen atom,
  - a $C_1-C_4$ alkyl radical.

According to one particular embodiment, the compound(s) of formula (I') are such that, when $Z''_1$ represents an oxygen atom, $R''_1$ denotes a linear or branched $C_1-C_6$ alkyl radical, a $C_1-C_6$ hydroxyalkyl radical; a di($C_1$-$C_4$ alkyl)amino($C_1$-$C_6$ alkyl) radical; a radical $-[(CH_2)_{m'}\text{-}O]_{p'}\text{-}L'Y'$ with $p'=1, 2, 3$, preferably 1 or 2, $m'=2$ or 3, L' denoting a saturated linear $C_1-C_6$ divalent hydrocarbon-based radical, and Y' denoting a hydroxyl radical or a hydrogen atom; an alkyl radical substituted with a heterocycle chosen from pyrrolidinyl, piperidinyl, morpholinyl, piperazinyl and imidazolyl, said heterocycle being optionally substituted with one or more $C_1-C_4$ alkyl radicals such as methyl, or hydroxyl. Better still, $R'_1$ denotes a linear or branched saturated $C_1-C_6$ alkyl radical, such as a methyl, ethyl, n-propyl, isopropyl or tert-butyl radical; a $C_1-C_6$ hydroxyalkyl radical such as a hydroxyethyl or hydroxypropyl radical; a dimethylaminoethyl or dimethylaminopropyl radical; a radical $-[(CH_2)_2-O]_{p'}\text{-}L'\text{-}Y'$ with $p'=1$ or 2, L' denoting a saturated, linear, $C_1-C_6$ divalent hydrocarbon-based radical, and Y' denoting a hydroxyl radical or a hydrogen atom such that -L'-Y' denotes an isopropyl or ethyl radical; or an ethyl or propyl radical substituted with a heterocycle chosen from pyrrolidinyl, piperidinyl, morpholinyl, piperazinyl and imidazolyl, said heterocycle being optionally substituted with one or more $C_1-C_4$ alkyl radicals such as methyl, or hydroxyl.

According to one particular embodiment of the invention, the compound(s) of formula (I') are such that, when $Z''_1$ represents NH, $R''_1$ denotes a $C_1-C_6$ hydroxyalkyl radical, a di($C_1-C_4$ alkyl)amino($C_1-C_6$ alkyl) radical, an alkyl radical substituted with a heterocycle chosen from pyrrolidinyl, piperidinyl, morpholinyl, piperazinyl and imidazolyl, said heterocycle being optionally substituted with one or more $C_1-C_4$ alkyl radicals such as methyl, or hydroxyl.

According to another embodiment, when $Z''_1$ represents $-N(R''_6)-$, $R''_1$ and $R''_6$ each independently denote a $C_1-C_6$ alkyl radical or a $C_1-C_6$ hydroxyalkyl radical, and preferably $R'_1$ and $R'_6$ are identical.

According to another embodiment, when $Z''_1$ is $-N(R''_6)-$ and $R''_1$ forms, with $R''_6$, a ring, this ring is chosen from piperazinyl, piperazinium, imidazolyl, pyrrolidinyl, pyridinyl, morpholinyl, morpholinium, piperidinyl, piperidinium, preferentially piperazinyl, piperazinium optionally substituted in particular with one or more $C_1-C_4$ alkyl groups such as methyl; piperazinium optionally substituted in particular with a $C_1-C_4$ alkyl group such as methyl.

The compounds of formula (I) are preferably dissymmetrical.

According to another embodiment, the compounds of formula (I) are symmetrical.

According to one particular embodiment of the invention, the compounds of formula (I) are cationic.

According to another particular embodiment of the invention, the compounds of formula (I) are non-cationic.

As examples of dyes of formula (I), mention may be made of the compounds presented below:

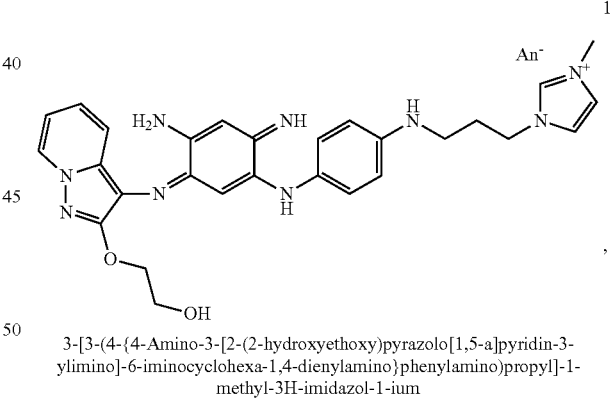

3-[3-(4-{4-Amino-3-[2-(2-hydroxyethoxy)pyrazolo[1,5-a]pyridin-3-ylimino]-6-iminocyclohexa-1,4-dienylamino}phenylamino)propyl]-1-methyl-3H-imidazol-1-ium

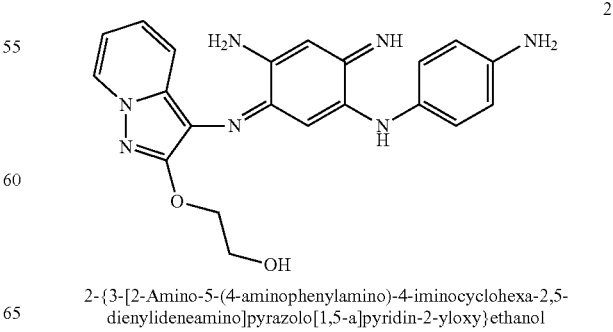

2-{3-[2-Amino-5-(4-aminophenylamino)-4-iminocyclohexa-2,5-dienylideneamino]pyrazolo[1,5-a]pyridin-2-yloxy}ethanol -continued

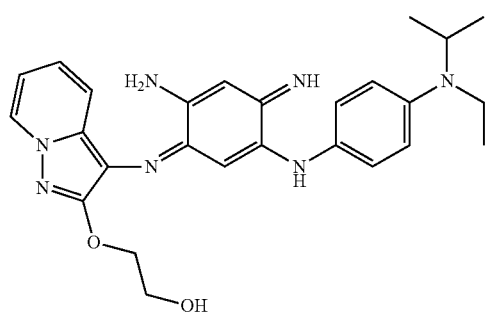

2-{3-[2-Amino-5-(4-ethylisopropylamino)phenylamino]-4-iminocyclohexa-2,5-dienylideneamino]pyrazolo[1,5-a]pyridin-2-yloxy}ethanol

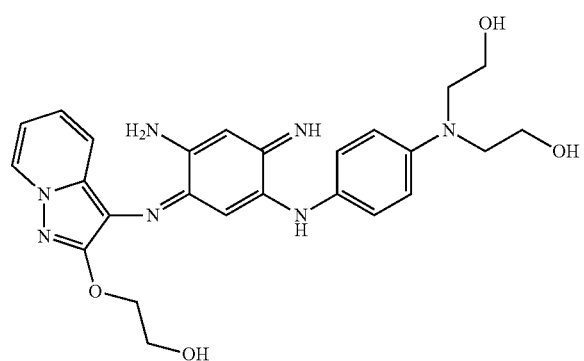

2-{3-[2-Amino-5-{4-[bis(2-hydroxyethyl)amino]phenylamino}-4-iminocyclohexa-2,5-dienylideneamino]pyrazolo[1,5-a]pyridin-2-yloxy}ethanol

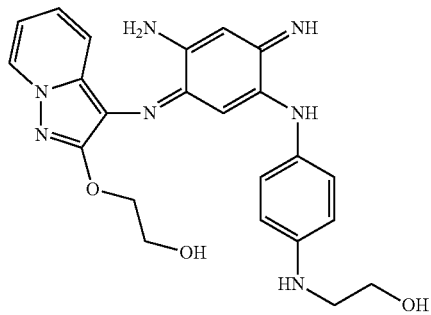

2-{3-[2-Amino-5-[4-(2-hydroxyethylamino)phenylamino]4-iminocyclohexa-2,5-dienylideneamino]pyrazolo[1,5-a]pyridin-2-yloxy}ethanol

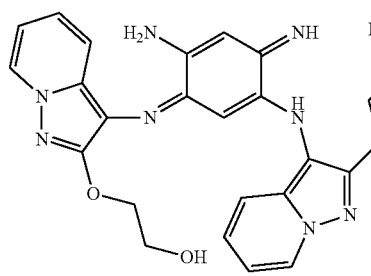

2-{3-[2-Amino-5-[2-(2-hydroxyethoxy)pyrazolo[1,5-a]pyridin-3-ylamino]-4-iminocyclohexa-2,5-dienylideneamino]pyrzolo[1,5-a]-pyridin-2-yloxy}ethanol -continued

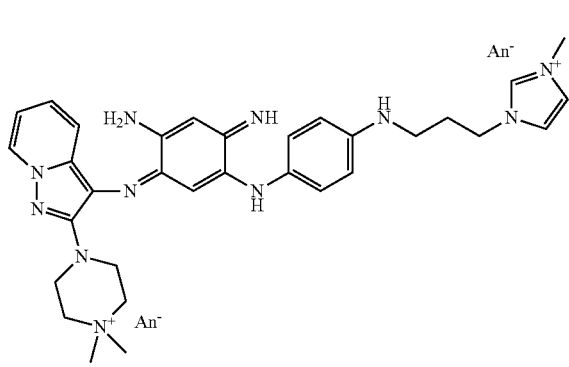

4-[3-({(2-amino-4-imino-5-[(4-{[3-(3-methyl-1H-imidazol-3-ium-1-yl)propyl]amino}phenyl)amino]cyclohexa-2,5-dien-1-ylidene}amino)pyrazolo[1,5-a]pyridin-2-yl]-1,1-dimethylpiperazin-1-ium, An⁻

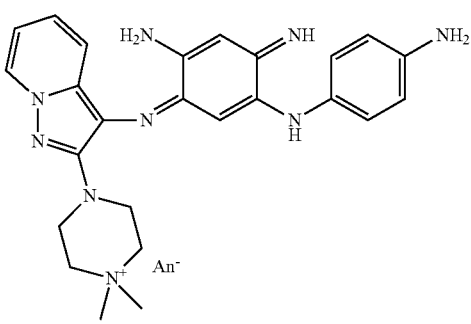

4-{3-[2-Amino-5-(4-aminophenylamino)-4-iminocyclohexa-2,5-dienylideneamino]pyrazolo[1.5-a]pyridin-2-yl}-1,1-dimethylpiperazin-1-ium, An⁻

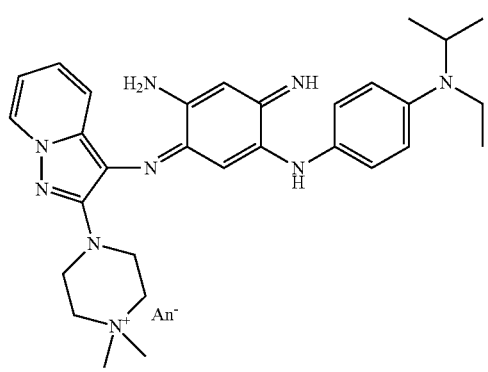

4-{3-[2-Amino-5-[4-(ethylisopropylamino)phenylamino]-4-iminocyclohexa-2,5-dienylideneamino]pyrazolo[1,5-a]pyridin-2-yl}-1,1-dimethylpiperazin-1-ium, An⁻

-continued

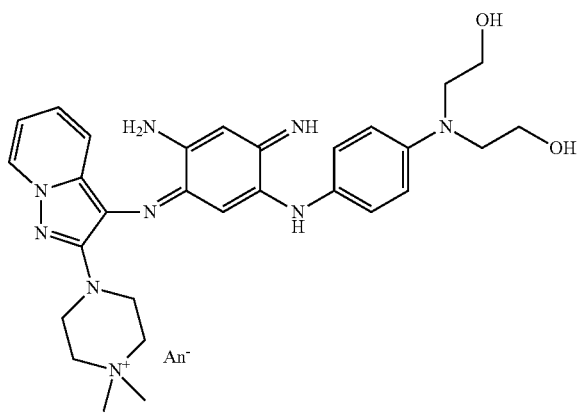

4-{3-[2-Amino-5-{4-[bis(2-hydroxyethyl)amino]phenylamino}-4-iminocyclohexa-2,5-dienylideneamino]pyrazolo[1,5-a]pyridin-2-yl}-1,1-dimethylpiperazin-1-ium, An⁻

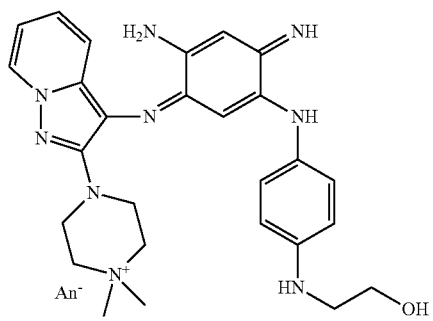

4-{3-[2-Amino-5-[4-(2-hydroxyethylamino)phenylamino]-4-iminocyclohexa-2,5-dienylideneamino]pyrazolo[1,5-a]pyridin-2-yl}-1,1-dimethylpiperazin-1-ium, An⁻

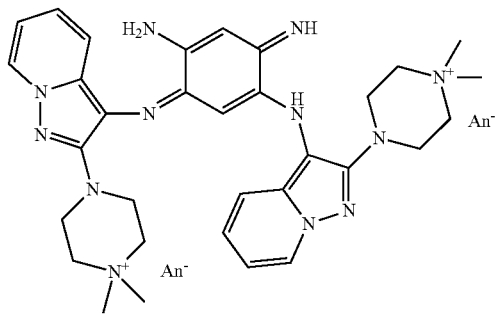

4-(3-{[(2-amino-5-{[2-(4,4-dimethylpiperazin-4-ium-1-yl)pyrazolo[1,5-a]pyridin-3-yl]amino}-4-iminocyclohexa-2,5-dien-1-ylidene]amino}pyrazolo[1,5-a]pyridin-2-yl)-1,1-dimethylpiperazin-1-ium, An⁻ and also the organic or mineral acid or base addition salts thereof, the leuco forms thereof, the geometrical isomers thereof, the tautomers thereof, and the solvates thereof such as hydrates, with An⁻, which may be identical or different, representing an anionic counterion; preferably compounds 1 to 6.

In the context of the invention, the term "derivative of formula (I)" is intended to mean all mesomeric, tautomeric or optical or geometrical isomer forms, or leuco forms.

The term "addition salts" is intended to mean the salts of physiologically acceptable organic or mineral acids of the compounds of formula (I).

The compounds of formula (I) may optionally be salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

Moreover, the addition salts that may be used in the context of the invention are also chosen from addition salts with a cosmetically acceptable base such as the basifying agents as defined below, for instance alkali metal hydroxides such as sodium hydroxide, potassium hydroxide, aqueous ammonia, amines or alkanolamines.

The compounds of formula (I) may also be in the form of solvates, for example a hydrate or a solvate of a linear or branched alcohol such as ethanol or isopropanol.

The present invention makes it possible in particular to rapidly obtain strong chromatic colorings that withstand the various attacking factors to which hair may be subjected, in particular shampoos and light.

The compounds of formula (I) are colored and coloring species.

The compounds of formula (I) are prepared from reagents available by conventional methods known to those skilled in the art or from commercial compounds.

Mention may for example be made of the preparation process according to the following synthesis schemes:
in the case where formulae (I) are symmetrical:
either starting from reagent $A_2$ of 3,4-diamino type:

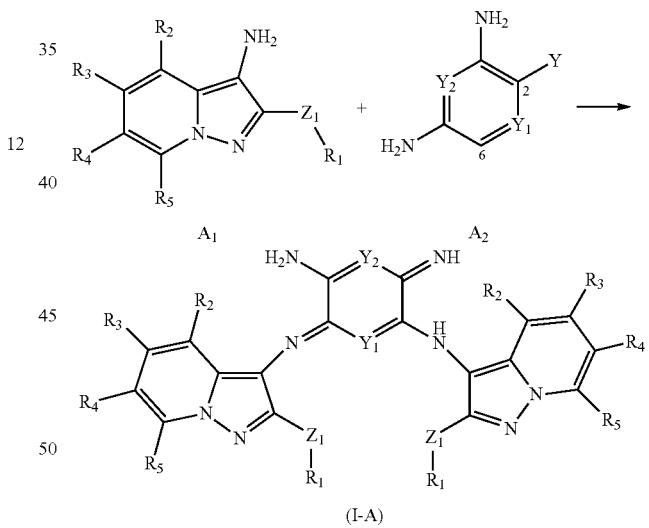

(I-A)

which consists:
in a first step, in reacting at least two molar equivalents of pyrazolo[1,5-a]pyridine compound $A_1$ comprising an amino group in position 3 with a reagent $A_2$ which is free in position 6 of the aromatic ring and comprising in position 2 a radical Y which is either a hydrogen atom or an electrofugal group,
preferably, this reaction is performed i) in a polar protic solvent such as in water or a mixture of water/$C_1$-$C_{10}$ alcohol such as ethanol, ii) and/or in the presence of one or more mineral or organic basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between ambient temperature, i.e. 25° C., and the reflux temperature of the solvent, preferably at ambient temperature; then in a second step, in maintaining the reaction medium under stirring for a time of between 5 minutes and 48 hours, more particularly between 30 minutes and 24 hours if the reaction is performed at ambient temperature; and then the reaction products (I-A) are optionally purified by a standard technique such as recrystallization, filtration or chromatography;

it being understood that, in formulae $A_1$, $A_2$ and (I-A), the radicals $R_1$, $Z_1$, $R_2$, $R_3$, $R_4$, $R_5$, $Y_1$ and $Y_2$ are as defined previously and that, when $Y_1$ represents NH then $Y_2$ cannot represent a CH group and Y represents a hydrogen atom or an electrofugal atom or group, preferably an electrofugal atom or group, such as halogen, (poly)halo($C_1$-$C_6$ alkoxy), or (poly)(halo)($C_1$-$C_6$ alkyl)-$SO_3$—;

or starting from reagent $A_4$ of 3,4-dinitro type:

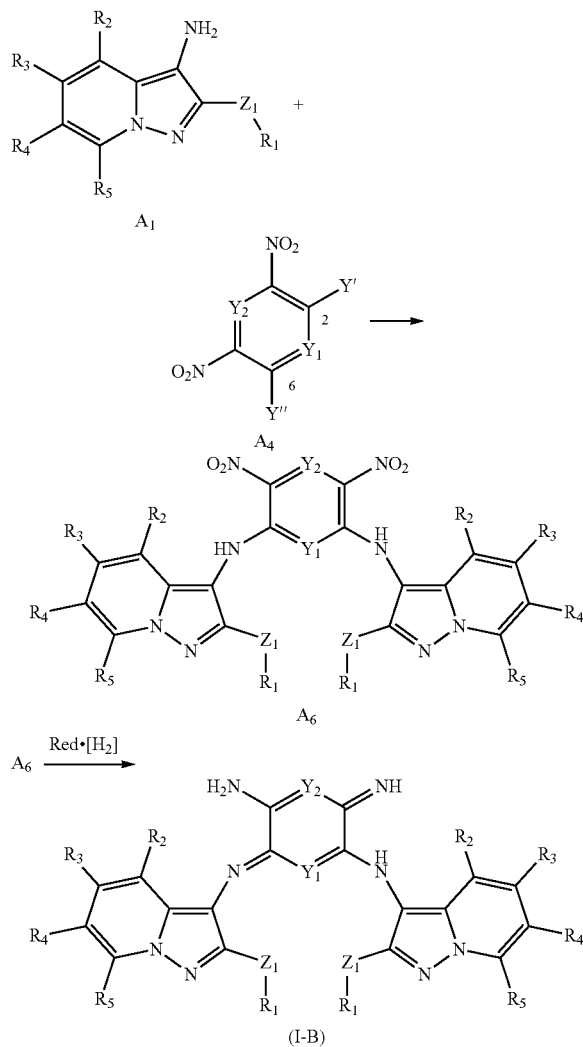

amino group in position 3 with a reagent $A_4$ comprising in position 2 and 6 of the aromatic ring an electrofugal atom or group; preferably, this reaction is performed i) in a polar protic solvent such as a $C_1$-$C_{10}$ alcohol such as ethanol, ii) and/or in the presence of one or more mineral or organic basifying agents, as defined below, chosen in particular from organic amines such as N,N-diisopropylethylamine, iii) preferably under an inert atmosphere; iv) and/or at a temperature between ambient temperature, i.e. 25° C., and the reflux temperature of the solvent, preferably at a temperature between 40° C. and 80° C.; then in a second step, in maintaining the reaction medium under stirring for a time of between 5 minutes and 48 hours, more particularly between 30 minutes and 24 hours if the reaction is performed at ambient temperature; and then the reaction product $A_6$ is optionally purified by a standard technique such as recrystallization, filtration or chromatography;

according to one variant, the compound $A_5$, once purified, is reduced preferably by catalysis under hydrogen, for example with palladium, nickel or zinc, preferably with zinc, in a polar protic solvent, in particular a $C_1$-$C_6$ alkanol such as butanol, in an acidic medium, preferably with a carboxylic acid such as acetic acid, so as to give the compounds (I) according to the invention optionally purified by a standard technique such as recrystallization, filtration or chromatography;

according to another variant, the compound $A_5$ is not purified, and is reduced preferably by catalysis under hydrogen, for example with palladium on graphite or nickel, in a polar protic solvent, in particular a $C_1$-$C_6$ alkanol such as methanol, so as to give the compounds (I) according to the invention optionally purified by a standard technique such as recrystallization, filtration or chromatography;

it being understood that $R_1$, $Z_1$, $R_2$, $R_3$, $R_4$, $R_5$, X, Y, $Y_1$ and $Y_2$ are as defined previously, and Y' and Y''', which may be identical or different, represent an electrofugal atom or group, such as halogen, (poly)halo($C_1$-$C_6$ alkoxy) or (poly)(halo)($C_1$-$C_6$alkyl)-$SO_3$—; and that, when $Y_1$ represents NH then $Y_2$ does not represent a CH group; preferably, $Y_1$ and $Y_2$ represent a group C(R) with R representing a hydrogen atom or a ($C_1$-$C_6$)alkyl group;

in the case where formulae (I) are symmetrical or dissymmetrical:
  either starting from reagent $A_2$ of 3,4-diamino type:

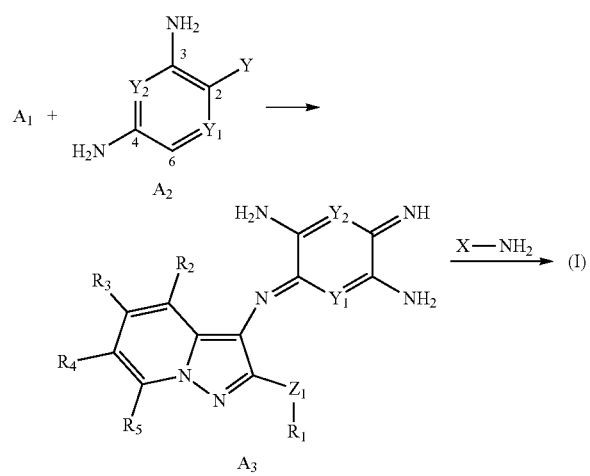

which consists:
  in a first step, in reacting at least two molar equivalents of pyrazolo[1,5-a]pyridine compound $A_1$ comprising an which consists:

in a first step, in reacting one molar equivalent of pyrazolo[1,5-a]pyridine compound $A_1$ comprising an amino group in position 3 with a reagent $A_2$ as defined previously;

preferably, this reaction is performed i) in a polar protic solvent such as in water or a mixture of water/$C_1$-$C_{10}$ alcohol such as ethanol, ii) and/or in the presence of one or more mineral or organic basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between ambient temperature, i.e. 25° C., and the reflux temperature of the solvent, preferably at ambient temperature; then in a second step, in maintaining the reaction medium under stirring for a time of between 5 minutes and 48 hours, more particularly between 30 minutes and 24 hours if the reaction is performed at ambient temperature; and then the reaction product $A_3$ is optionally purified by a standard technique such as recrystallization, filtration or chromatography;

according to one variant, the compound $A_3$, once purified, reacts with one molar equivalent of a reagent bearing a (hetero)aryl group comprising a primary amine X—$NH_2$ under the same conditions as steps 1) and 2), to give the products (I), which are optionally purified by a standard technique such as recrystallization, filtration or chromatography;

according to another variant, the compound $A_3$ is not purified, and reacts with one molar equivalent of the primary amine X—$NH_2$ an amino group, under the same conditions as steps a) and b), to give the products (I), which are optionally purified by a standard technique such as recrystallization, filtration or chromatography;

it being understood that $R_1$, $Z_1$, $R_2$, $R_3$, $R_4$, $R_5$, X, Y, $Y_1$ and $Y_2$ are as defined previously, Y' and Y'' represent an atom or group and that, when $Y_1$ represents NH and $Y_2$ represents a CH group, then X represents a group other than a pyrazolo[1,5-a]pyridin-3-yl group which is optionally substituted;

or starting from reagent $A_4$ of 3,4-dinitro type:

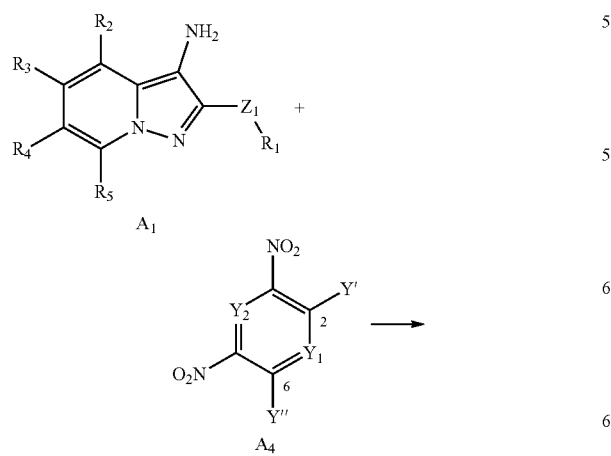

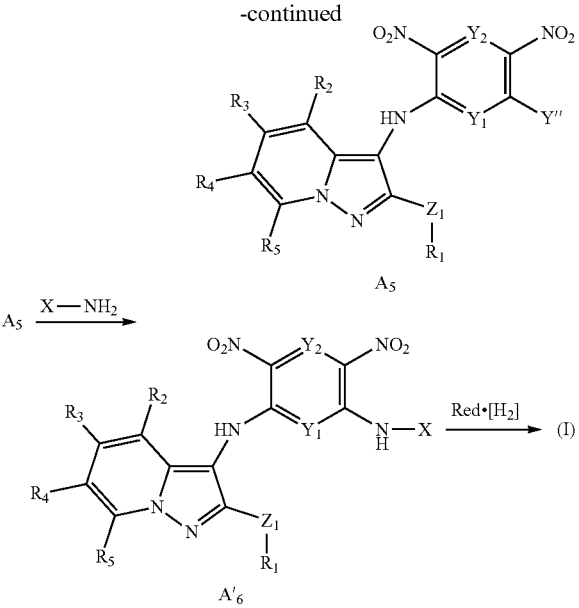

which consists:

in a first step, in reacting one molar equivalent of pyrazolo[1,5-a]pyridine compound $A_1$ comprising an amino group in position 3 with a reagent $A_4$ comprising in position 2 and 6 of the aromatic ring an electrofugal atom or group; preferably, this reaction is performed i) in a polar protic solvent such as a $C_1$-$C_{10}$ alcohol such as ethanol, ii) and/or in the presence of one or more mineral or organic basifying agents, as defined below, chosen in particular from organic amines such as N,N-diisopropylethylamine, iii) preferably under an inert atmosphere; iv) and/or at a temperature between ambient temperature, i.e. 25° C., and the reflux temperature of the solvent, preferably at ambient temperature; then in a second step, in maintaining the reaction medium under stirring for a time of between 5 minutes and 48 hours, more particularly between 30 minutes and 24 hours if the reaction is performed at ambient temperature; and then the reaction product $A_5$ is optionally purified by a standard technique such as recrystallization, filtration or chromatography;

according to one variant, the compound $A_5$, once purified, reacts with one molar equivalent of a reagent bearing a (hetero)aryl group comprising a primary amine X—$NH_2$ in a polar aprotic heteroaromatic solvent such as N-methylpyrrolidine, preferably under an inert atmosphere, by heating at a temperature greater than or equal to 50° C., preferably between 80° C. and 120° C., to give the products $A_6$ optionally purified by a standard technique such as recrystallization, filtration or chromatography;

according to another variant, the compound $A_5$ is not purified, and reacts with one molar equivalent of the primary amine X—$NH_2$ in a polar aprotic heteroaromatic solvent such as N-methylpyrrolidine, preferably under an inert atmosphere, by heating at a temperature greater than or equal to 50° C., preferably between 60° C. and 120° C., to give the products $A'_6$ optionally purified by a standard technique such as recrystallization, filtration or chromatography;

in a final step, $A'_6$ is reduced preferably by catalysis under hydrogen, for example with palladium on graphite or nickel, in a polar protic solvent, in particular a $C_1$-$C_6$ alkanol such as methanol, to give the compounds (I) according to the invention;

it being understood that $R_1$, $Z_1$, $R_2$, $R_3$, $R_4$, $R_5$, X, Y, $Y_1$ and $Y_2$ are as defined previously, and Y' and Y", which may be identical or different, represent an electrofugal atom or group, such as halogen, (poly)halo($C_1$-$C_6$ alkoxy) or (poly) (halo)($C_1$-$C_6$alkyl)-$SO_3$—; and that, when $Y_1$ represents NH and $Y_2$ represents a CH group, then X represents a group other than a pyrazolo[1,5-a]pyridin-3-yl group which is optionally substituted. Preferably, the preparation process which makes use of the reagent $A_4$ is used when $Y_1$ and $Y_2$ represent a group C(R) with R representing a hydrogen atom or a ($C_1$-$C_6$)alkyl group.

When the synthesis involves the dinitro reagents $A_4$, the reduction methods described during the final step are known; mention may for example be made of Advanced Organic Chemistry, 4th ed., 1992 J. MARCH, WILEY Interscience; *Reduction in Organic Chemistry*, M. Hudlicky, 1983, Ellis Honwood series Chemical Science.

The compounds ($A_6$) and ($A'_6$) can be obtained by substitution of dihalodinitrobenzene with aromatic or heteroaromatic amines according to Synthesis 1990 (12), 1147-1148 and *Synth Commun* 1990, 20(22), 3537-3543.

More particularly, the compounds of formula (I) may be obtained according to the procedure described below.

In a reactor, compound $A_1$ is dissolved in water and/or ethanol at ambient temperature. Compound $A_2$ is then added, followed by a base such as ammonia, sodium hydroxide, potassium hydroxide, a mineral carbonate such as potassium carbonate, or a sodium or potassium or ammonium acetate in the presence of an oxidizing agent. The oxidizing agent may be air, aqueous hydrogen peroxide solution or any other chemical oxidizing agent. The reaction medium becomes colored as soon as the last two reagents are added. The reaction medium thus obtained is stirred for a time of from 30 minutes to 6 days. The product formed is filtered off and then washed with water and then optionally with isopropyl ether. The compound recovered in powder form is dried at 20° C. under vacuum to constant weight. In the case where there is no precipitation, the compound resulting from this reaction is recovered by evaporating off the solvent and optionally purified on a column of silica.

In a reactor, compound $A_1$ is dissolved in a solvent of $C_1$-$C_6$ alkanol type such as ethanol, with stirring. $A_1$ can be synthesized according to the methods known by those skilled in the art; mention may for example be made of FR2892924. The medium is then placed under an inert atmosphere such as Ar or nitrogen, then an alkaline agent is added, preferably an organic alkaline agent, such as N,N-diisopropylethylamine (2.1 molar eq.), followed by the reagent $A_4$ as defined previously (1 molar eq.), preferably 1,5-dichloro-2,4-dinitrobenzene. $A_5$ can be purified by precipitation from a polar protic-type solvent of $C_1$-$C_6$ alkanol type such as ethanol, and filtration, and then the solvent is evaporated off. A mixture of (hetero)aryl comprising a primary amine group X—$NH_2$ (1.2 molar eq.) and of heteroaromatic solvent of polar aprotic type, such as N-methylpyrrolidinone, in the presence of an alkaline agent, preferably an organic amine, such as N,N-diisopropylethylamine (3.2 eq.) is then added to $A_5$ (1 molar eq.). The medium is heated at a temperature greater than 60° C., preferably around 100° C. The progression of the reaction is preferably monitored by TLC. Compound $A_6$ can then be purified by means of a standard method, in particular precipitation, before undergoing reduction by catalysis with palladium on graphite, in the presence of hydrogen, in a polar protic solvent of $C_1$-$C_4$ alkanol type such as methanol, so as to give the compound (I) according to the invention. The reaction can be monitored by HPLC and/or by TLC. The compound (I) can be purified by means of a standard method such as filtration, recrystallization, and/or chromatography, in particular on alumina.

The characterization is performed by NMR spectroscopy and/or mass spectrometry.

A subject of the present invention is also a composition for dyeing keratin fibers, comprising, in a medium that is suitable in particular for dyeing keratin fibers such as the hair, at least one compound chosen from the compounds of formulae (I) or (I') as defined previously, and also the leuco forms, optical isomers, geometrical isomers and tautomers thereof, and also the acid or base addition salts thereof, and the solvates thereof such as hydrates.

According to one particular embodiment of the invention, the compound(s) of formula (I) or (I') as defined previously represent from 0.01% to 15%, more particularly from 0.05% to 10% by weight, preferentially from 0.1% to 5%, relative to the total weight of the composition.

The dye composition of the invention may be in various forms, such as in the form of liquids, creams or gels, or in any other form that is suitable for dyeing keratin fibers, and in particular human hair.

Another subject of the invention is a process for dyeing keratin fibers, in particular human keratin fibers such as the hair, by applying to said fibers the cosmetic composition which comprises at least one dye of formula (I) or (I') as defined previously.

The composition that is useful in the context of the invention may furthermore comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines, examples that may be mentioned more particularly include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis((3-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-((3-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 2-(2,5-diaminophenyl)ethanol, 2-(methoxymethyl)benzene-1,4-diamine, 3-(2,5-diaminophenyl)propan-1-ol and 1-{3-[(4-aminophenyl)amino]propyl}-3-methyl-1H-imidazol-3-ium chloride, and the acid addition salts thereof.

Among the para-phenylenediamines mentioned above, para-phenylenediamine, para-tolylenediamine, 2-isopropylpara-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, 2-(2,5-diaminophenyl)ethanol, 2-(methoxymethyl)benzene-1,4-diamine, 3-(2,5-diaminophenyl)propan-1-ol and 1-{3-[(4-aminophenyl)amino]propyl}-3-methyl-1H-imidazol-3-ium chloride, and the acid addition salts thereof, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols, examples that may be mentioned include 2-aminophenol, 2-amino-5-methylphenol, 2-amino-6-methylphenol and 5-acetamido-2-aminophenol, and the acid addition salts thereof.

Among the heterocyclic bases, examples that may be mentioned include pyridine derivatives, pyrimidine derivatives and pyrazole derivatives, and derivatives of pyrazolo[1,2-a]pyrazol-1-one type and derivatives of pyrazolopyridine type as described in European patent applications Nos 1 792 903 and 1 792 606.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidine derivatives, mention may be made of the compounds described, for example, in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

Among the derivatives of pyrazolo[1,2-a]pyrazol-1-one type, mention may be made of compounds such as 2,3-diamino-6,7-dihydro,1H-5H-pyrazolo[1,2-a]pyrazol-1-one.

The composition that is useful in the context of the invention may also contain one or more couplers that are conventionally used for dyeing keratin fibers. Among these couplers, mention may be made in particular of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the acid addition salts thereof.

In general, the acid addition salts that may be used in the context of the invention for the oxidation bases and the couplers are in particular chosen from the hydrochlorides, hydrobromides, sulfates, citrates, succinates, tartrates, lactates, tosylates, benzenesulfonates, phosphates and acetates.

When the oxidation base(s) are present in the dye composition according to the invention, their amount preferably ranges from 0.001% to 10% by weight and more preferentially from 0.005% to 6% by weight relative to the total weight of the composition.

When they are present, the coupler(s) are generally present in an amount ranging from 0.001% to 10% by weight and more preferentially from 0.005% to 6% by weight relative to the total weight of the composition.

The composition that is useful in the context of the invention may optionally comprise at least one additional direct dye conventionally used for the dyeing of keratin fibers. It may be chosen from cationic or nonionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanin dyes, triarylmethane-based dyes and natural dyes, alone or as mixtures.

It may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl) aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine and 1-amino-2-nitro-4-hydroxy-5-methylbenzene.

The additional direct dye may also be chosen from yellow and green-yellow nitrobenzene direct dyes. Examples that may be mentioned include the compounds chosen from: 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis ((3-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Mention may also be made of blue or violet nitrobenzene direct dyes, for instance 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl-N-β-hydroxyethyl)amino-2-nitrobenzene, 1-(β-hydroxyethyl) amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, and the 2-nitro-para-phenylenediamines of formula (III) below:

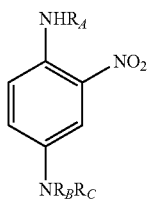

(III)

in which formula (III):
$R_B$ represents a $C_1$-$C_4$ alkyl radical or a β-hydroxyethyl, β-hydroxypropyl or γ-hydroxypropyl radical;
$R_A$ and $R_C$, which may be identical or different, represent a β-hydroxyethyl, β-hydroxypropyl, γ-hydroxypropyl or β,γ-dihydroxypropyl radical, at least one of the radicals $R_B$, $R_C$ or $R_A$ representing a γ-hydroxypropyl radical and $R_B$ and $R_C$ not being able simultaneously to denote a β-hydroxyethyl radical when R is a γ-hydroxypropyl radical.

These compounds of formula (III) can be found in French patent FR 2 692 572.

Among the azo direct dyes that can be used according to the invention, mention may be made of the cationic azo dyes described in patent applications WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369 and FR 2 844 269.

Among these compounds, mention may be made most particularly of the following dyes: 1,3-dimethyl-2-[[4-(dimethylamino)phenyl]azo]-1H-imidazolium halides, 1,3-dimethyl-2-[(4-aminophenyl)azo]-1H-imidazolium halides, 1-methyl-4-[(methylphenylhydrazono)methyl]pyridinium halides or alkyl sulfates.

Among the azo direct dyes that may also be mentioned are the following dyes, described in the Color Index International, 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes, mention may be made of the following compounds: Basic Blue 17, Basic Red 2.

Among the triarylmethane dyes that can be used according to the invention, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds: 2-β-hydroxyethylamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-β'-chloro-4'-methylamino)phenylureido-6-methyl-1,4-benzoquinoneimine and 3-[4'-N-(ethylcarbamylmethyl)amino]phenylureido-6-methyl-1, 4-benzoquinoneimine.

Among the dyes of tetraazapentamethine type that may be used according to the invention, mention may be made of the following compounds: 2-((E)-{(E)-[(1,3-dimethyl-1,3-dihydro-2H-imidazol-2-ylidene)hydrazono]
methyl}diazenyl)-1,3-dimethyl-1H-imidazol-3-ium chloride; 2-{(E)-[(1Z)—N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2(1H)-ylidene)hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)pyridinium chloride; 1-(2-hydroxyethyl)-2-[(E)-((1E)-1-{(2E)-[1-(2-hydroxyethyl)pyridin-2(1H)-ylidene]hydrazono}ethyl)diazenyl]pyridinium chloride; 1-methyl-2-((E)-{(E)-[(2Z)-(1-methylpyridin-2(1H)-ylidene)hydrazono]methyl}diazenyl)pyridinium chloride; 1-(2-hydroxyethyl)-2-[(E)-((E)-{(2E)-[1-(2-hydroxyethyl)pyridin-2(1H)-ylidene]hydrazono}methyl)diazenyl]pyridinium acetate.

Among the additional natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and in particular henna-based poultices or extracts.

When they are present, the content of additional direct dyes in the composition generally ranges from 0.001% to 20% and preferably from 0.01% to 10% by weight relative to the weight of the composition.

The medium that is suitable for dyeing, also known as the dye support, generally comprises water or a mixture of water and of at least one organic solvent to dissolve the compounds that are not sufficiently water-soluble.

More particularly, the organic solvents are chosen from linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, in particular of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

The dye composition that is useful in the context of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

These above adjuvants are generally present in an amount, for each of them, of between 0.01% and 20% by weight relative to the weight of the composition.

Needless to say, those skilled in the art will take care to select this or these optional additional compound(s) such that the advantageous properties intrinsically associated with the dye composition that is useful in the context of the invention are not, or are not substantially, adversely affected by the envisaged addition(s).

The pH of the dye composition that is useful in the context of the invention is generally between 3 and 12 approximately and preferably between 5 and 11 approximately. It can be adjusted to the desired value by means of acidifying or basifying agents regularly used in the dyeing of keratin fibers or alternatively using conventional buffer systems. Modifying the pH within these ranges will promote the formation of compounds (I) or (I').

Among the acidifying agents, examples that may be mentioned include mineral acids, for instance hydrochloric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (IV) below:

(IV)

in which formula (IV):
W is a $(C_1$-$C_6)$alkylene group, preferably a propylene group, optionally substituted with a hydroxyl group or a $C_1$-$C_4$ alkyl radical;
$R_a$, $R_b$, $R_c$ and $R_d$, which may be identical or different, represent a hydrogen atom or a $C_1$-$C_4$ alkyl or $C_1$-$C_4$ hydroxyalkyl radical.

The oxidizing agent will also be necessary for obtaining simultaneous lightening of the keratin fibers (lightening dyeing) and/or when the composition contains oxidation bases or couplers.

The composition according to the invention may also contain one or more oxidizing agents.

The oxidizing agent may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The oxidizing agent will preferably be hydrogen peroxide.

In the case where the oxidizing agent(s) are present in the dye composition according to the invention, their amount will preferably range from 5% to 100% by weight and better still from 50% to 100% by weight relative to the total weight of the composition.

The dye composition that is useful in the context of the invention may be in various forms, such as in the form of liquids, creams or gels, or in any other form that is suitable for dyeing keratin fibers, and in particular human hair.

A subject of the present invention is also the use of the compounds according to the invention, chosen from the compounds of formulae (I) and (I') as defined previously, and also the leuco forms, optical isomers, geometrical isomers and tautomers thereof, and the acid or base addition salts thereof and the solvates thereof, for dyeing keratin fibers, in particular human keratin fibers such as the hair.

The dyeing process of the invention comprises the application to the keratin fibers of at least one dye composition as defined above.

When an oxidizing agent is used, it may be present in the composition of the invention. It may also be applied separately, as a pretreatment or post-treatment.

The application of the composition of the invention may optionally be followed by rinsing.

The leave-on time for the dye composition is generally between 3 and 60 minutes, preferably between 5 and 40 minutes and even more preferentially between 10 and 30 minutes.

The application temperature generally used is ambient temperature, preferably between 25 and 55° C.

A subject of the present invention is also a multi-compartment device or kit for performing the process for dyeing keratin fibers, described above.

The examples that follow serve to illustrate the invention without, however, being limiting in nature.

EXAMPLES

I) Examples of Synthesis

Compound (1): Synthesis of 3-[3-(4-{4-amino-3-[2-(2-hydroxyethoxy)pyrazolo[1,5-a]pyridin-3-ylimino]-6-iminocyclohexa-1,4-dienylamino}phenylamino)propyl]-1-methyl-3H-imidazol-1-ium chloride (1)

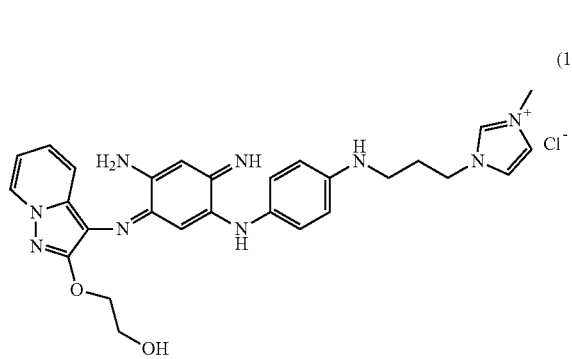

(1)

a) Synthesis of 2-[3-(5-chloro-2,4-dinitrophenylamino)pyrazolo[1,5-a]pyridin-2-yloxy]ethanol (1a)

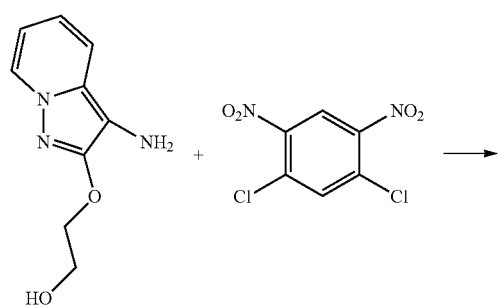

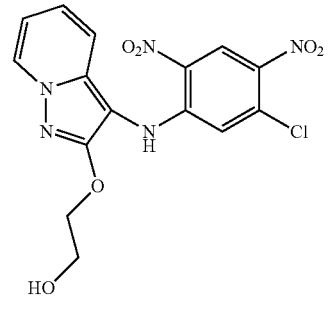

(1a)

In a 100 ml three-necked flask with magnetic stirring and equipped with a thermometer, 2-β-aminopyrazolo[1,5-a]pyridin-2-yloxy)ethanol (synthesis described in FR2892924) (2.13 g, 9.3 mmol, 1.1 eq) is dissolved in ethanol (20 ml). The medium is placed under argon and then N,N-diisopropylethylamine (3.1 ml, 17.7 mmol; 2.1 eq) is added, followed by 1,5-dichloro-2,4-dinitrobenzene (2 g, 8.4 mmol, 1 eq).

A precipitate forms and 40 ml of ethanol are added. After stirring for 3 h at ambient temperature, the medium is filtered on sintered glass and the precipitate is then dried in a desiccator ($P_2O_5$, vacuum, 45° C.). The compound (1a) is obtained in the form of an orange powder. The NMR and mass analyses are in accordance with the expected structure (1a).

b) Synthesis of 3-[3-(4-{5-[2-(2-hydroxyethoxy) pyrazolo[1,5-a]pyridin-3-ylamino]-2,4-dinitrophenylamino}phenylamino)propyl]-1-methyl-3H-imidazol-1-ium chloride (1b)

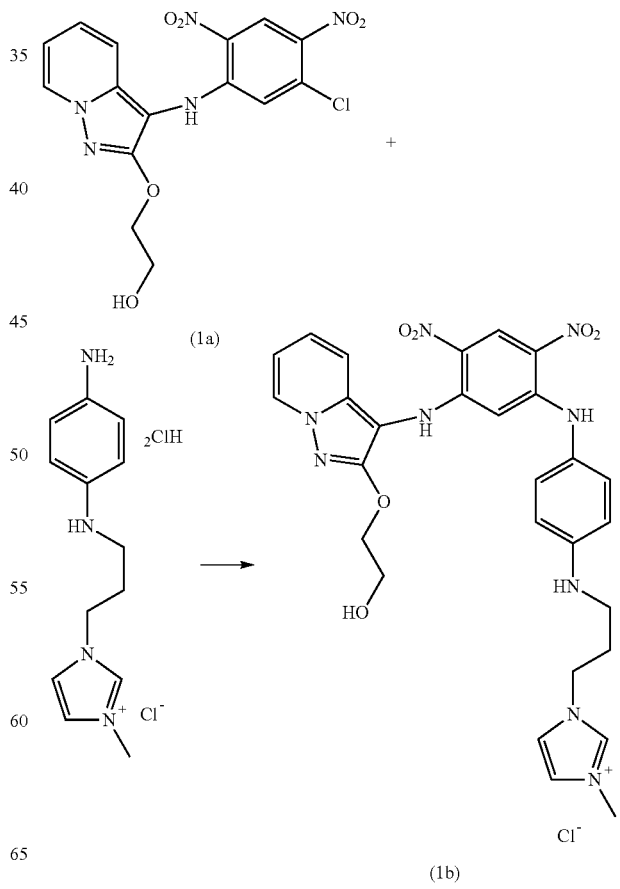

(1b)

170 μl of N,N-diisopropylethylamine (3.2 eq) and then 500 mg (1 eq) of compound (1a) are added, under an argon atmosphere, to a solution of 390 mg of [3-(4-aminophenylamino)propyl]-1-methyl-3H-imidazol-1-ium dihydrochloride chloride (1.2 eq) in 3 ml of N-methylpyrrolidinone. The medium is heated to 100° C. and the reaction is monitored by TLC (CH$_2$Cl$_2$/MeOH 98/2). After 1 h 30 at 100° C., the medium is cooled to ambient temperature and then poured onto 50 ml of isopropanol. The precipitate formed is filtered off on sintered glass so as to give, after trituration from diisopropyl ether and drying (P$_2$O$_5$, vacuum, 45° C.), the compound (1b) obtained in the form of a black powder. The NMR and mass analyses are in accordance with the expected structure (1b).

c) Synthesis of 3-[3-(4-{4-amino-3-[2-(2-hydroxyethoxy)pyrazolo[1,5-a]pyridin-3-ylimino]-6-iminocyclohexa-1,4-dienylamino}phenylamino)propyl]-1-methyl-3H-imidazol-1-ium chloride (1)

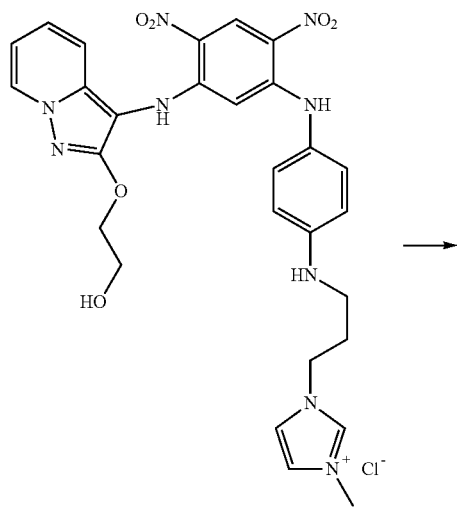

(1b)

(1)

In a 100 ml three-necked flask equipped with a thermometer and with an argon inlet, 512 mg of nitro compound (1b) (1 eq) and 512 mg of palladium-on-carbon at 5% are added to 10 ml of methanol. The medium is heated to 60° C. and then 414 mg of ammonium formate (8 eq) are added fractionwise with a spatula.

The reaction is verified by HPLC and by TLC. When there is no more nitro compound, the reaction medium is filtered on sintered glass with a bed of celite and then the filtrate is evaporated to dryness.

The solid obtained is then purified on a neutral alumina column, eluted with a mixture of dichloromethane and methanol (100/0 to 60/40 in 45 min). The expected product (1) is obtained in the form of a black powder. The NMR and mass analyses are in accordance with the expected structure (1).

Compound (2): Synthesis of 2-{3-[2-amino-5-(4-aminophenylamino)-4-iminocyclohexa-2,5-dienylideneamino]pyrazolo[1,5-a]pyridin-2-yloxy}ethanol (2)

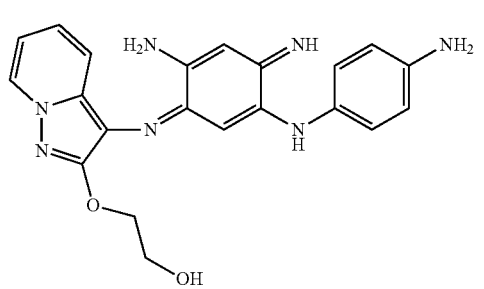

(2)

a) Synthesis of 2-{3-[5-(4-aminophenylamino)-2,4-dinitrophenylamino]pyrazolo[1,5-a]pyridin-2-yloxy}ethanol (2b)

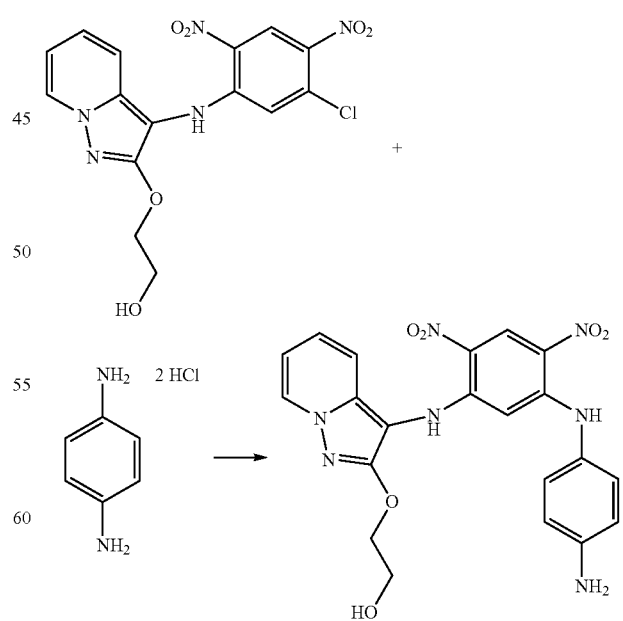

(2b)

2.8 ml of N,N-diisopropylethylamine (2.2 eq) and then 3 g (1 eq) of compound (1a) obtained according to the procedure described in example 1 are added, under an argon atmosphere, to a solution of 2.8 g of para-phenylenediamine dihydrochloride (1.2 eq) in 35 ml of N-methylpyrrolidinone. The medium is heated to 75° C. and the reaction is monitored by TLC (CH₂Cl₂/MeOH 98/2).

After 3 h at 75° C., the reaction medium is cooled to ambient temperature and then poured onto ice. The precipitate obtained is filtered off on sintered glass so as to give, after trituration from diisopropyl ether and then drying (P₂O₅, vacuum, 45° C.), the compound (2b) obtained in the form of a red powder. The NMR and mass analyses are in accordance with the expected structure (2b).

b) Synthesis of 2-{3-[2-amino-5-(4-aminophenylamino)-4-iminocyclohexa-2,5-dienylideneamino]pyrazolo[1,5-a]pyridin-2-yloxy}ethanol (2)

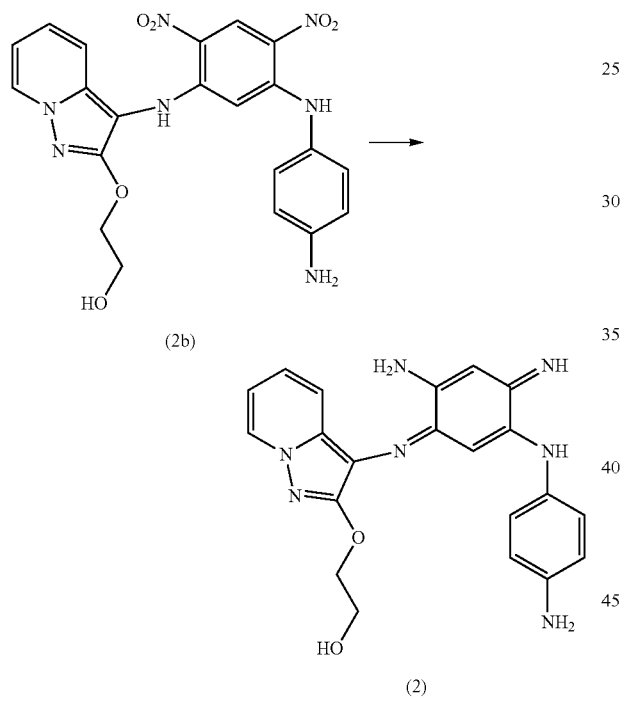

In a 100 ml three-necked flask equipped with a thermometer and with an argon inlet, 700 mg of nitro compound (2b) (1 eq) and 700 mg of palladium-on-carbon at 5% are added to 12 ml of methanol. The medium is heated to 60° C. and then 759 mg of ammonium formate (8 eq) are added fractionwise with a spatula.

The reaction is verified by HPLC and by TLC. At the end of the reaction, the reaction medium is filtered on sintered glass with a bed of celite and then the filtrate is evaporated to dryness.

The solid obtained is then purified on a neutral alumina column, eluted with a mixture of dichloromethane and methanol (100/0 to 60/40 in 45 min).

The expected product (2) is obtained in the form of a black powder. The NMR and mass analyses are in accordance with the expected structure (2).

Compound (3): Synthesis of 2-{3-[2-amino-5-[4-(ethylisopropylamino)phenylamino]-4-iminocyclohexa-2,5-dienylideneamino]pyrazolo[1,5-a]pyridin-2-yloxy}ethanol (3)

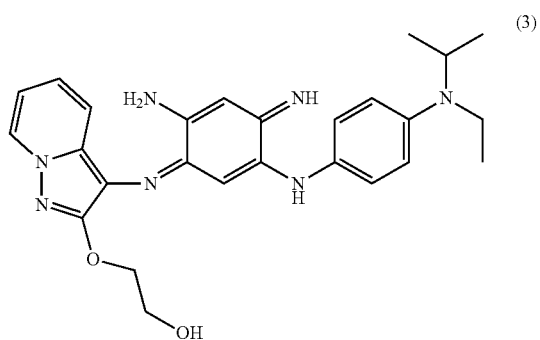 [SMILES: CCN(c1ccc(NC2=C/C(=N/c3c(OCCO)nn4ccccc34)C(N)=CC2=N)cc1)C(C)C]

a) Synthesis of 2-(3-{5-[4-(isopropylmethylamino)phenylamino]-2,4-dinitrophenylamino}pyrazolo[1,5-a]pyridin-2-yloxy)ethanol (3b)

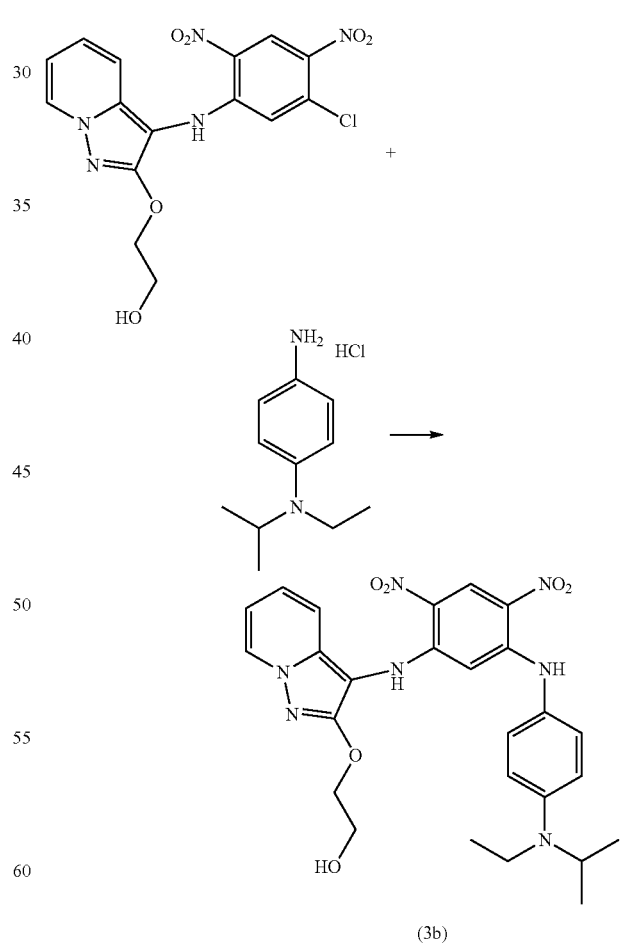

1.8 ml of N,N-diisopropylethylamine (4.1 eq) and then 2.8 g (1 eq) of compound (1a) as described in example 1 are added, under an argon atmosphere, to a solution of 1.83 g of N-ethyl-N-isopropyl para-phenylenediamine hydrochloride (1.2 eq) in 50 ml of N-methylpyrrolidinone. The medium is heated to 100° C. and the reaction is monitored by TLC (CH$_2$Cl$_2$/MeOH 98/2).

After 2 h 30 at 100° C. and cooling to ambient temperature, the reaction medium is poured onto ice. The precipitate obtained is filtered off on sintered glass so as to give, after trituration from diisopropyl ether and drying (P$_2$O$_5$, vacuum, 45° C.), the compound (3b) isolated in the form of a brown powder. The NMR and mass analyses are in accordance with the expected structure (3b).

b) Synthesis of 2-{3-[2-amino-5-[4-(ethylisopropylamino)phenylamino]-4-iminocyclohexa-2,5-dienylideneamino]pyrazolo[1,5-a]pyridin-2-yloxy}ethanol (3)

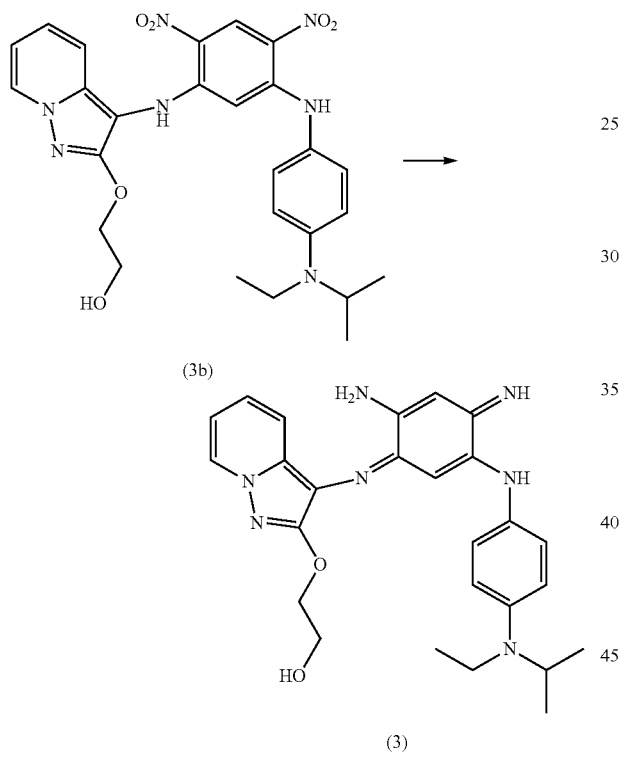

In a 100 ml three-necked flask equipped with a thermometer and with an argon inlet, 1 g of nitro compound (3b) (1 eq) and 1 g of palladium-on-carbon at 5% are added to 12 ml of methanol. The medium is heated to 60° C. and then 941 mg of ammonium formate (8 eq) are added fractionwise with a spatula.

The reaction is verified by HPLC and by TLC. When there is no more nitro compound, the reaction medium is filtered on sintered glass with a bed of celite and then the filtrate is evaporated to dryness.

The solid obtained is then purified on a neutral alumina column, eluted with a mixture of dichloromethane and methanol (100/0 to 60/40 in 45 min).

The expected product (3) is thus obtained in the form of a black powder. The NMR and mass analyses are in accordance with the expected structure (3).

Compound (4): Synthesis of 2-{3-[2-amino-5-{4-[bis(2-hydroxyethyl)amino]phenylamino}-4-iminocyclohexa-2,5-dienylideneamino]pyrazolo[1,5-a]pyridin-2-yloxy}ethanol (4)

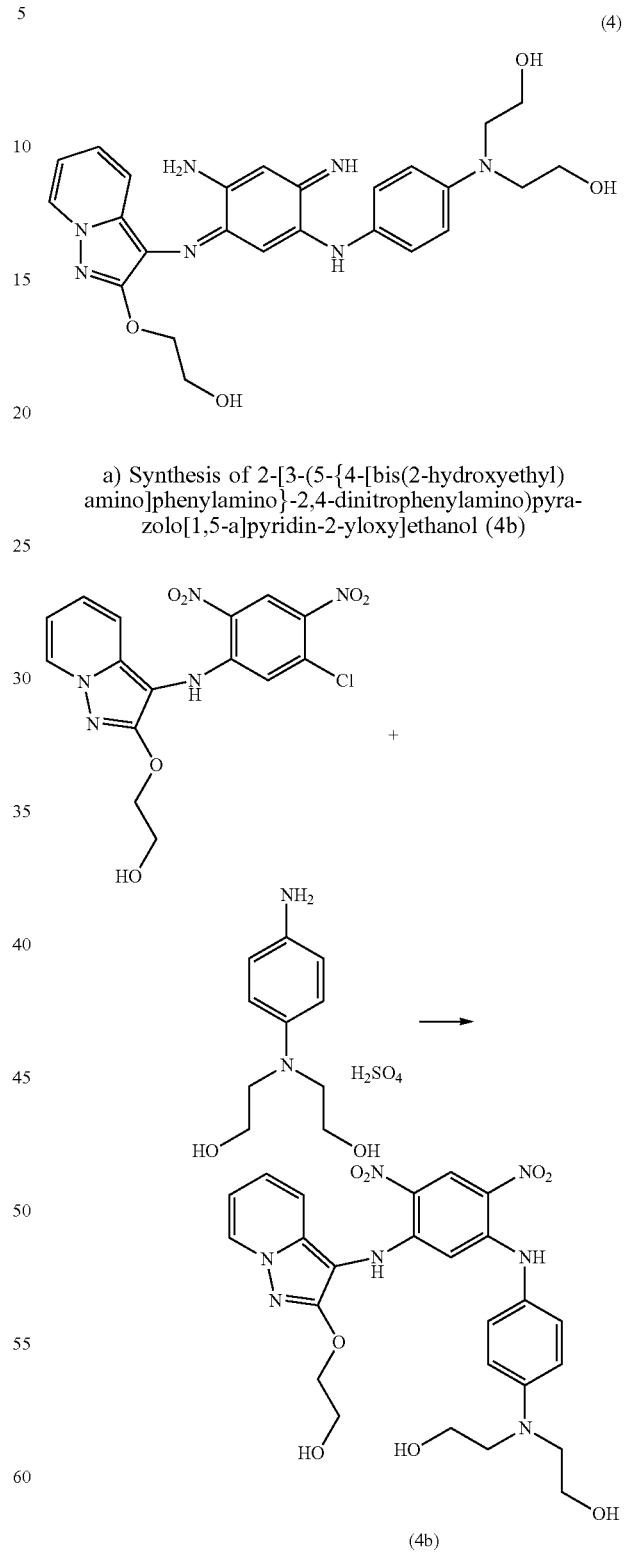

a) Synthesis of 2-[3-(5-{4-[bis(2-hydroxyethyl)amino]phenylamino}-2,4-dinitrophenylamino)pyrazolo[1,5-a]pyridin-2-yloxy]ethanol (4b)

4.2 ml of N,N-diisopropylethylamine (3.2 eq) are added, under an argon atmosphere, to a solution of 2.9 g of N,N-2-hydroxyethyl para-phenylenediamine sulfate (1.2 eq)

in 40 ml of N-methylpyrrolidinone, and then 3 g (1 eq) of compound (1a) previously described in example 1 are added. The medium is heated to 100° C. and the reaction is monitored by TLC (CH$_2$Cl$_2$/MeOH 98/2).

After 2 h at 100° C., the reaction medium is poured onto ice and the precipitate obtained is filtered off on sintered glass so as to give, after trituration from diisopropyl ether and then drying (P$_2$O$_5$, vacuum, 45° C.), the compound (4b) isolated in the form of an orange powder.

The NMR and mass analyses are in accordance with the expected structure (4b).

b) Synthesis of 2-{3-[2-amino-5-{4-[bis(2-hydroxy-ethyl)amino]phenylamino}-4-iminocyclohexa-2,5-dienylideneamino]pyrazolo[1,5-a]pyridin-2-yloxy}ethanol (4)

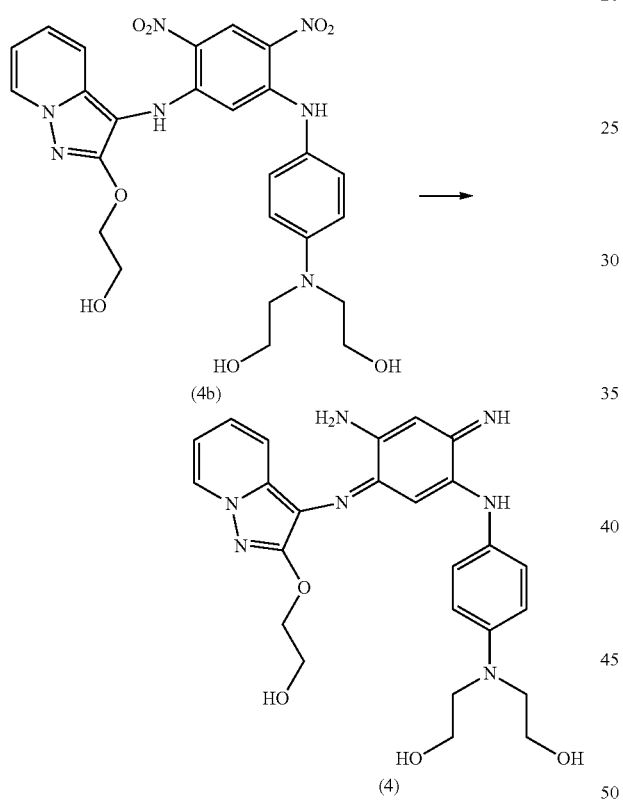

In a 100 ml three-necked flask equipped with a thermometer and with an argon inlet, 1 g of nitro compound (4b) (1 eq) and 1 g of palladium-on-carbon at 5% are added to 12 ml of methanol. The medium is heated to 60° C. and then 941 mg of ammonium formate (8 eq) are added fractionwise with a spatula. The reaction is verified by HPLC and by TLC. When there is no more nitro compound, the reaction medium is filtered on sintered glass with a bed of celite and then the filtrate is evaporated to dryness. The solid obtained is then purified on a neutral alumina column, eluted with a mixture of dichloromethane and methanol (100/0 to 60/40 in 45 min).

The expected product (4) is obtained in the form of a black powder. The NMR and mass analyses are in accordance with the expected structure (4).

Compound (5): Synthesis of 2-{3-[2-amino-5-[4-(2-hydroxyethylamino)phenylamino]-4-iminocyclohexa-2,5-dien-(Z)-ylideneamino]pyrazolo[1,5-a]pyridin-2-yloxy}ethanol (5)

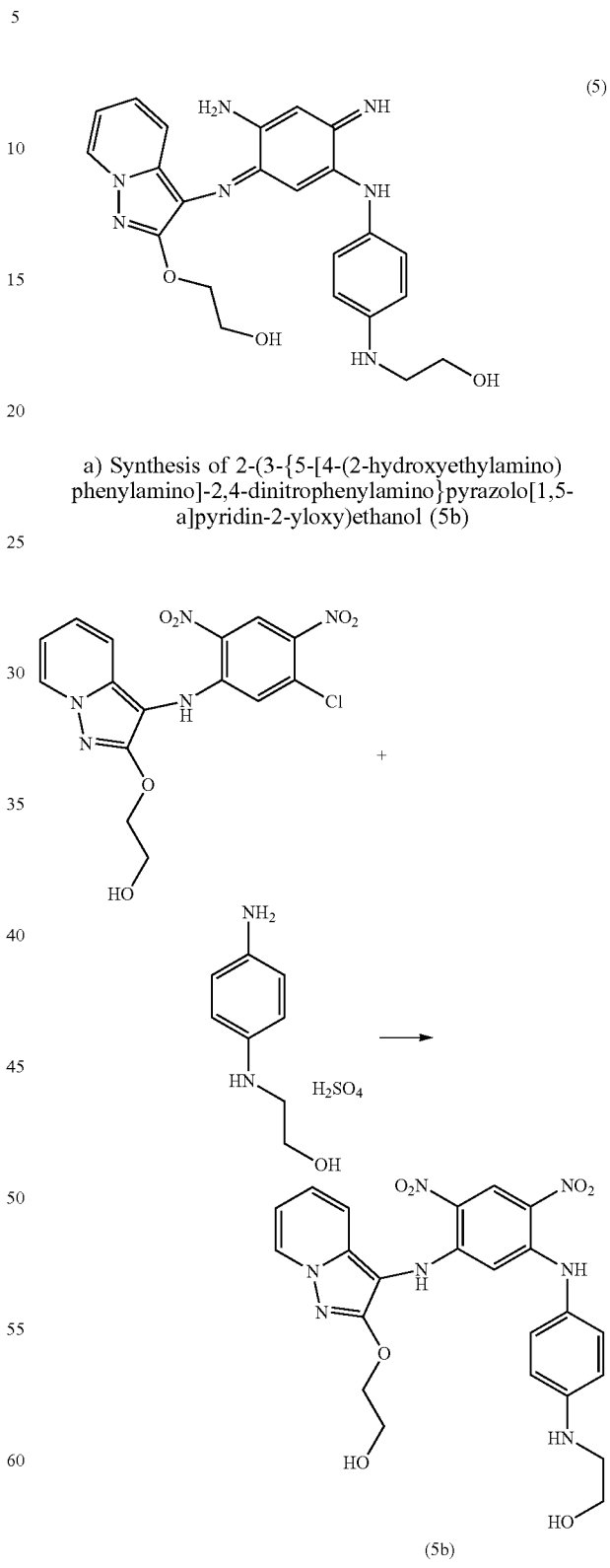

a) Synthesis of 2-(3-{5-[4-(2-hydroxyethylamino)phenylamino]-2,4-dinitrophenylamino}pyrazolo[1,5-a]pyridin-2-yloxy)ethanol (5b)

4.6 ml of N,N-diisopropylethylamine (3.5 eq) and then 3 g (1 eq) of compound (1a) previously described in example 1 are added, under an argon atmosphere, to a solution of 2.28 g of N,2-hydroxyethyl para-phenylenediamine sulfate (1.2 eq) in 40 ml of N-methylpyrrolidinone. The medium is heated to 100° C. and the reaction is monitored by TLC (CH$_2$Cl$_2$/MeOH 98/2).

After 2 h 30 at 100° C., the reaction medium is poured onto ice. The precipitate obtained is filtered off on sintered glass so as to give, after trituration from diisopropyl ether and then drying (P$_2$O$_5$, vacuum, 45° C.), the compound (5b) isolated in the form of an orange powder.

The NMR and mass analyses are in accordance with the expected structure (5b).

b) Synthesis of 2-{3-[2-amino-5-[4-(2-hydroxyethylamino)phenylamino]-4-iminocyclohexa-2,5-dienylideneamino]pyrazolo[1,5-a]pyridin-2-yloxy}ethanol (5)

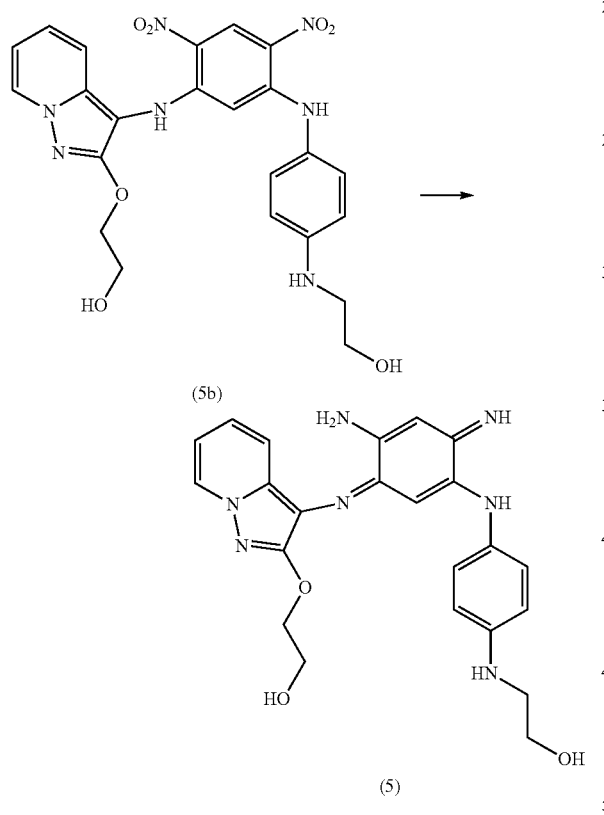

In a 100 ml three-necked flask equipped with a thermometer and with an argon inlet, 1 g of nitro compound (5b) (1 eq) and 1 g of palladium-on-carbon at 5% are added to 12 ml of methanol. The medium is heated to 60° C. and then 1.24 g of ammonium formate (10 eq) are added fractionwise with a spatula.

The reaction is verified by HPLC and by TLC. When there is no more nitro compound, the reaction medium is filtered on sintered glass with a bed of celite and then the filtrate is evaporated to dryness.

The solid obtained is then purified on a neutral alumina column, eluted with a mixture of dichloromethane and methanol (100/0 to 60/40 in 45 min). The expected product (5) is thus obtained in the form of a black powder. The NMR and mass analyses are in accordance with the expected structure (5).

Compound (6): Synthesis of 2-{3-[2-amino-5-[2-(2-hydroxyethoxy)pyrazolo[1,5-a]pyridin-3-ylamino]-4-iminocyclohexa-2,5-dienylideneamino]pyrazolo[1,5-a]pyridin-2-yloxy}ethanol (6)

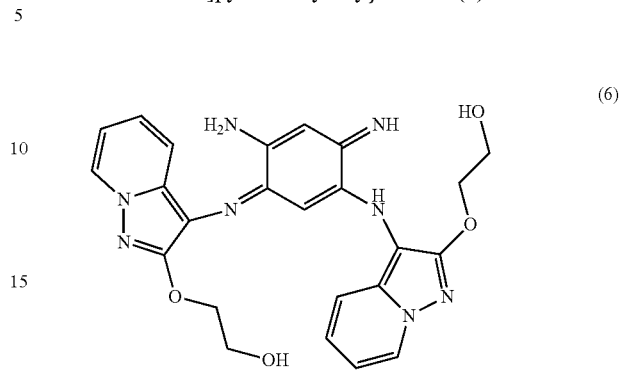

a) Synthesis of 2-(3-{5-[2-(2-hydroxyethoxy)pyrazolo[1,5-a]pyridin-3-ylamino]-2,4-dinitrophenylamino}pyrazolo[1,5-a]pyridin-2-yloxy)ethanol (6b)

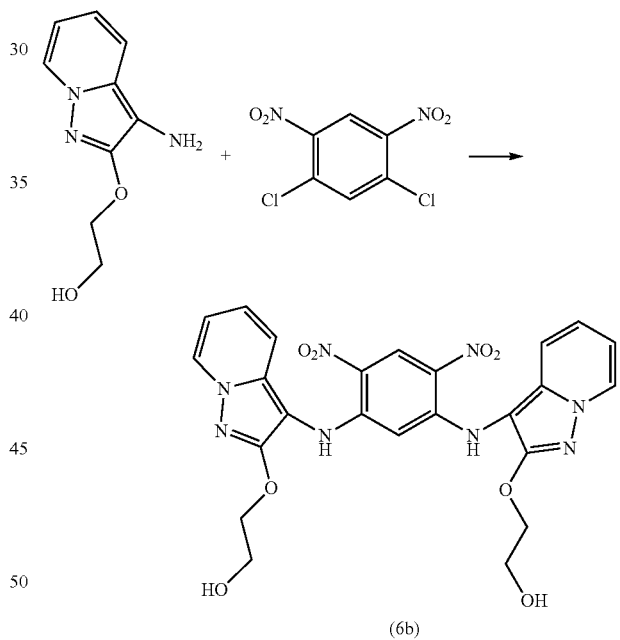

In a 100 ml three-necked flask equipped with a thermometer, 2-β-aminopyrazolo[1,5-a]pyridin-2-yloxy)ethanol (4.9 g, 21.2 mmol, 2.6 eq) is dissolved in N-methylpyrrolidinone (20 ml) with stirring. The medium is placed under argon and then N,N-diisopropylethylamine (6.7 ml, 38.9 mmol; 4.1 eq) is added, followed by 1,5-dichloro-2,4-dinitrobenzene (2 g, 8.4 mmol, 1 eq) before being brought to 50° C. After 3 h of stirring at 50° C., the reaction medium is poured onto 400 ml of ice.

The precipitate obtained is filtered off on sintered glass and then rinsed with water before being dried (P$_2$O$_5$, vacuum, 45° C.) so as to give the compound (6b) (orange powder).

b) Synthesis of 2-{3-[2-amino-5-[2-(2-hydroxy-ethoxy)pyrazolo[1,5-a]pyridin-3-ylamino]-4-imino-cyclohexa-2,5-dienylideneamino]pyrazolo[1,5-a]pyridin-2-yloxy}ethanol (6)

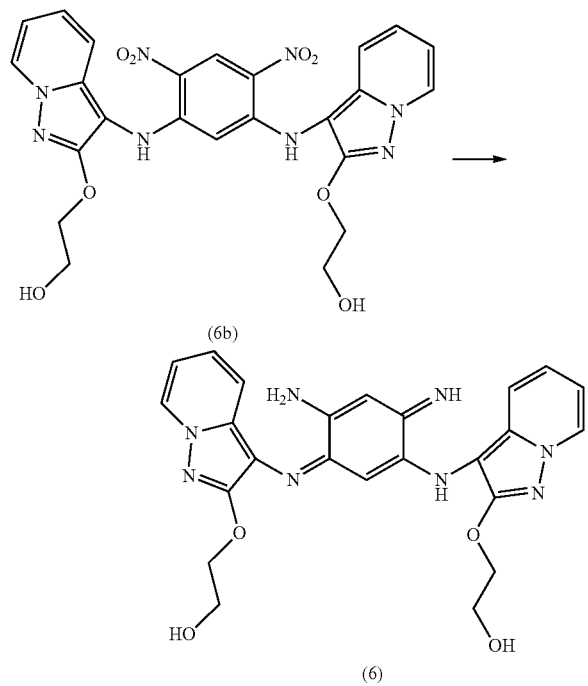

(6b)

(6)

In a 100 ml three-necked flask with magnetic stirring, equipped with a thermometer, 1 g of powdered zinc is suspended in 20 ml of butanol. The medium is heated to 100° C. and 100 µl of acetic acid are added, followed by 1 g of compound (6b).

The reaction is monitored by TLC and 100 µl of acetic acid are added after 1 h of reaction, followed by 300 µl 2 h later.

After cooling to ambient temperature, the precipitate formed is filtered off on sintered glass, and rinsed with ethanol and then ether. The gray powder obtained is placed in a three-necked flask containing 20 ml of HCl, iPrOH 5-6 N. The new precipitate obtained is then filtered off on sintered glass, before being taken up with methanol. The solution is concentrated to dryness under vacuum, taken up in ethyl ether, and then filtered on sintered glass and dried ($P_2O_5$, vacuum, 45° C.), giving the compound (6) (black powder). The NMR and mass analyses are in accordance with the expected structure (6).

II) Examples of Dyeing Keratin Fibers

The evaluation was carried out on locks of 1 g of natural Caucasian hair comprising 90% gray hair (NG). Each dye was tested at a concentration of 0.5% by weight in a formula containing 80% of water, 15% of ethanol and 5% of benzyl alcohol. The dye composition was applied to the keratin fibers, with a leave-on time of 30 min.

Rinsing with water was carried out, followed by shampooing and again rinsing with water.

Evaluation on a Spectrocolorimeter

The values L*a*b* were measured with a Minolta CM-3610d spectrophotometer and exploited with the Spectra Magix NX software.

In this L* a* b* system, the three parameters denote, respectively, L*: the color intensity, a*: the green/red color axis, and b*: the blue/yellow color axis. For the intensity, the lower the value, the darker and more intense the color.

The variation in coloring or gain in color build-up is the difference in color between the locks of natural gray hair (NG) treated with the composition according to the invention, and the untreated locks, and is measured by (4E) according to the following equation:

$$\Delta E = \sqrt{(L^*-L_o^*)^2+(a^*-a_o^*)^2+(b^*-b_o^*)^2}$$

In this equation, L*, a* and b* represent the values measured on NG dyed hair according to the invention, and $L_o^*$, $a_o^*$ and $b_o^*$ represent the values measured on the untreated locks.

The higher the value of ΔE, the greater the gain in color build-up.

| compound | L | a | b | ΔE |
|---|---|---|---|---|
| (1) | 26.69 | 4.22 | 2.72 | 37.61 |
| (2) | 29.55 | 4.56 | 4 | 34.55 |
| (4) | 30.46 | 5.08 | 1.86 | 34.41 |
| (5) | 25.21 | 4.1 | 2.86 | 35.00 |
| (6) | 34.4 | 3.24 | 4.35 | 29.70 |

It appears, according to the values above, that the color build-up is very satisfactory on the keratin fibers, this being whatever the type of dye of the invention.

III) Examples of Dyeing Keratin Fibers—Comparative Tests

1/Preparation of the Compositions

The following dyeing compositions B, C, D, E, F (according to invention) and A (comparative) were prepared from the ingredients listed in the table below. The contents are expressed as a percentage of active material relative to the total weight of the composition.

Comparative Compound 1

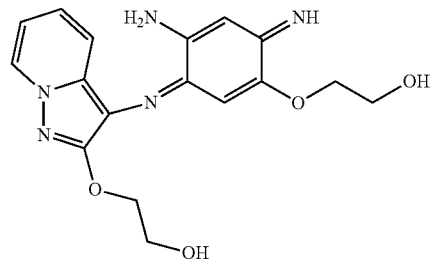

Invention Compound (1)

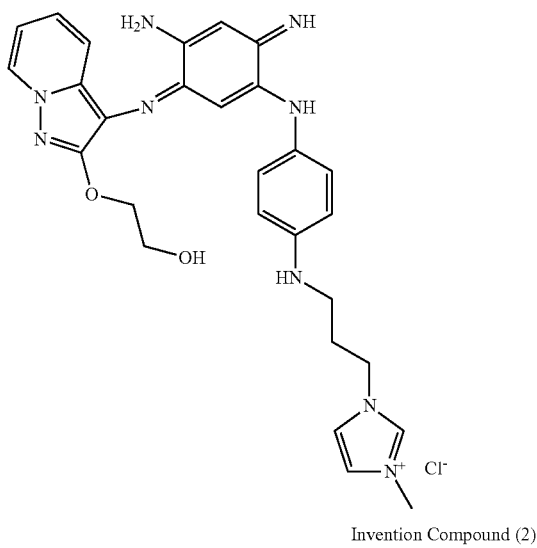

Invention Compound (2)

Invention Compound (4)

Invention Compound (5)

Invention Compound (6)

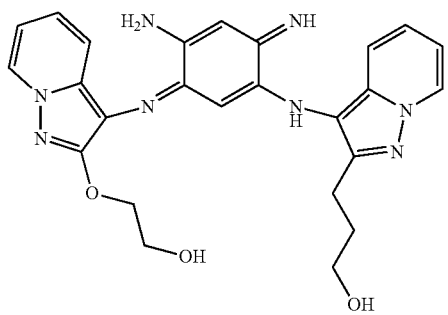

| Compositions | A (comp) | B (inv) | C (inv) | D (inv) | E (inv) | F (inv) |
|---|---|---|---|---|---|---|
| Compound 1 | 0.5 g | — | — | — | — | — |
| Compound (6) | — | 0.5 g | — | — | — | — |
| Compound (2) | — | — | 0.5 g | — | — | — |
| Compound (5) | — | — | — | 0.5 g | — | — |
| Compound (1) | — | — | — | — | 0.5 g | — |
| Compound (4) | — | — | — | — | — | 0.5 g |
| Pure ethyl alcohol | 15 g | 15 g | 15 g | 15 g | 15 g | 15 g |
| Benzylic alcohol | 5 g | 5 g | 5 g | 5 g | 5 g | 5 g |
| Water | 79.5 g | 79.5 g | 79.5 g | 79.5 g | 79.5 g | 79.5 g |

The evaluation was carried out on locks of 1 g of natural Caucasian hair comprising 90% gray hair (NG). Each composition A to F was tested. The dye composition was applied to the keratin fibers, with a leave-on time of 30 min. Rinsing with water was carried out, followed by shampooing and again rinsing with water. The values L*a*b* were measured with a Minolta CM-3610d spectrophotometer and exploited with the Spectra Magix NX software.

Results

|  | a* | b* | Colour of hair after treatment |
|---|---|---|---|
| Composition A - Comparative | 9.36 | −2.37 | Purple |
| Composition B - Invention | 3.24 | 4.35 | Gray |
| Composition C - Invention | 4.56 | 4 | Brown |
| Composition D - Invention | 4.1 | 2.86 | Brown |
| Composition E - Invention | 4.22 | 2.72 | Brown |
| Composition F - Invention | 5.08 | 1.86 | Brown |

The results obtained show that the invention makes it possible to obtain color data a* and b* between 0 and 5.5 contrary to the comparative example composition A. Invention makes it possible to obtain gray, and brown colorations with a single direct dye, without the use of a mixture of hair dyes of different colours. Colours obtained with dyes of the invention are very esthetic and natural looking.

The invention claimed is:

1. A compound chosen from azomethine dyes comprising at least one pyrazolopyridine unit of formula (I), a leuco form, an optical isomer, a geometrical isomer, a tautomers thereof, an organic or mineral acid or base addition salt thereof, a solvate thereof, or a hydrate thereof:

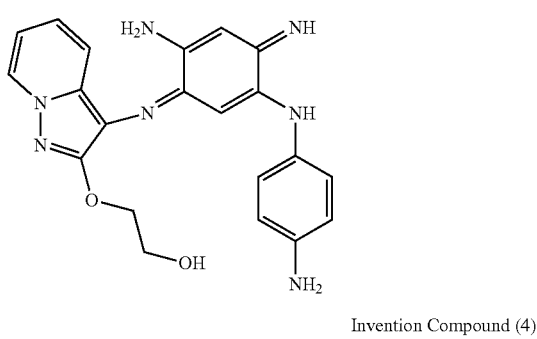

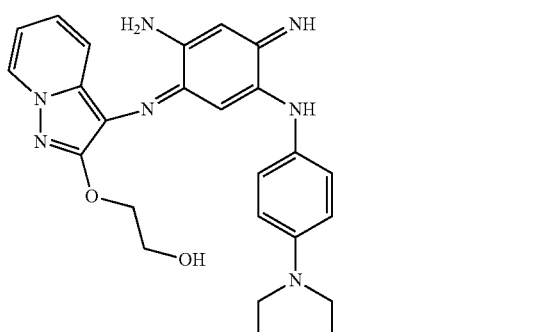

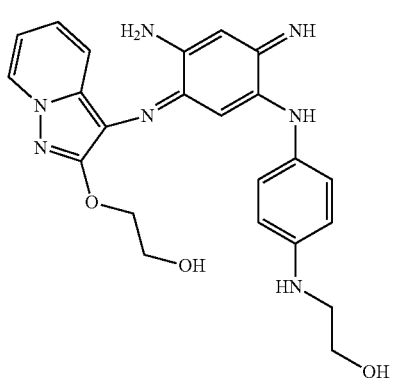

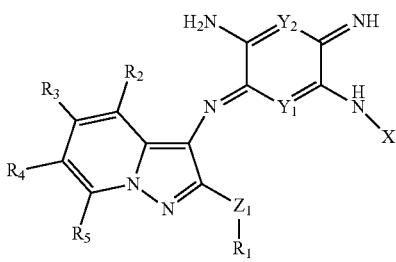

(I)

in which formula (I):
  $Y_1$ and $Y_2$, which may be identical or different, represent a nitrogen atom or a group C(R) with R representing a hydrogen atom or a $(C_1-C_6)$alkyl group;
  $Z_1$ represents an oxygen atom or a group —N($R_6$)—;
  when $Z_1$ represents —N($R_6$)—, then $R_1$ and $R_6$ optionally form, together with the nitrogen atom to which they are attached, an optionally substituted, optionally cationic, 5- to 8-membered, saturated, unsaturated or aromatic heterocycle;
  $R_1$ and $R_6$, which may be identical or different, represent:
    a hydrogen atom;
    a $C_1-C_{10}$ alkyl radical optionally interrupted with one or more non-adjacent heteroatoms, and/or optionally substituted;
    an optionally substituted, 5- to 8-membered, cationic or non-cationic, saturated, unsaturated or aromatic (hetero)cyclic radical;
  $R_2$, $R_3$, $R_4$, and $R_5$, which may be identical or different, each independently represent:
    a hydrogen atom;
    an optionally substituted $C_1-C_6$ alkyl radical;
    a group chosen from —$NH_2$, —N(H)$R_{10}$, —N($R_{11}$)$R_{12}$, OH and/or —O$R_9$, with $R_9$ and $R_{10}$ representing an optionally substituted, linear or branched $C_1-C_6$ alkyl, $R_{11}$ and $R_{12}$, which may be identical or different, representing an optionally substituted, linear or branched $C_1-C_6$ alkyl, wherein $R_{11}$ and $R_{12}$ optionally form, together with the nitrogen atom to which they are attached, a saturated, unsaturated or aromatic 5- to 8-membered heterocycle optionally containing one or more other heteroatoms or groups chosen from N, O, S, S(O)$_2$ and C(O), the heterocycle being optionally substituted;
    a halide and/or
  $R_2$, $R_3$, $R_4$, and $R_5$ form, in pairs, with adjacent radicals, an optionally substituted, saturated or unsaturated (hetero)cycle;
  X represents an optionally substituted aryl or optionally substituted heteroaryl radical;
  wherein
    when the compounds of formula (I) are cationic, then their electro-neutrality is provided by one or more cosmetically acceptable anions which may be identical or different; and
    when $Y_1$ represents NH and $Y_2$ represents a CH group, then X represents a group other than a pyrazolo[1,5-a]pyridin-3-yl group which is optionally substituted.

2. The compound of claim 1, wherein $Y_1$ represents N and $Y_2$ represents C(R).

3. The compound of claim 1, wherein $Y_1$ and $Y_2$ represent a group C(R).

4. The compound of claim 1, wherein X represents a group chosen from those of formula (II) or of formula (III):

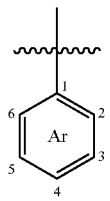

(II)

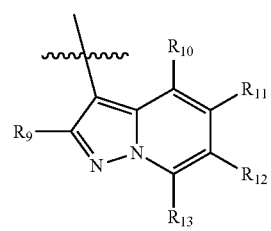

(III)

in which formulae (II) and (III):
  ‿‿‿ corresponds to the point of anchorage of the group (II) or (III) to the rest of the molecule;
  Ar represents an aryl group optionally substituted with one or more radicals $R_8$, which may be identical or different, $R_8$ representing an atom or group chosen from:
    halogen;
    —O$R'_{14}$;
    —N$R_{14}R_{15}$;
    $C_1-C_6$ alkyl optionally substituted with one or more atoms or groups, which may be identical or different, chosen from i) hydroxyls, ii) amino, iii) $(C_1-C_6)$alkylamino, iv) di$(C_1-C_6)$alkylamino, v) halogen, vi) $(C_1-C_6)$alkylimidazolyl, v) tri$(C_1-C_6)$alkylammonium $An^-$, vi) $(C_1-C_6)$alkylimidazolium $An^-$, vii) $(C_1-C_6)$alkylpyridinium $An^-$, viii) $(C_1-C_6)$alkylpiperidinium $An^-$;
    carboxyl (—C(O)—OH);
    carboxamide (—C(O)—N$R^aR^b$) with $R^a$ and $R^b$, which may be identical or different, representing a hydrogen atom or a $(C_1-C_4)$alkyl group; and
  $R_9$ represents:
    a radical —OR's; or
    a radical —N$R'_6R'_7$;
    when $R_9$ represents —N$R'_6R'_7$ then $R'_6$ and $R'_7$ can form, together with the nitrogen atom to which they are attached, an optionally substituted, optionally cationic, 5- to 8-membered, saturated, unsaturated or aromatic heterocycle;
    $R'_6$ and $R'_7$, which may be identical or different, represent:
      a hydrogen atom;
      a $C_1-C_{10}$ alkyl radical optionally interrupted with one or more non-adjacent heteroatoms, and/or optionally substituted with one or more groups chosen from i) hydroxyl, ii) optionally substituted, 5- to 8-membered, cationic or non-cationic, saturated, unsaturated or aromatic (hetero)cycle, iii) —N(R')R", iv) —$N^+$R'R"R'" with R', R" and R'" each independently representing a $C_1-C_6$ alkyl group;

an optionally substituted, 5- to 8-membered, cationic or non-cationic, saturated, unsaturated or aromatic (hetero)cyclic radical;

$R_{10}$, $R_{11}$, $R_{12}$ and $R_{13}$, which may be identical or different, represent:
  a hydrogen atom;
  an optionally substituted $C_1$-$C_4$ alkyl radical;
  a group chosen from —$NH_2$, —$N(H)R_{16}$, —$N(R_{17})R_{18}$, OH and —$OR_{19}$, with $R_{16}$ and $R_{19}$ independently representing an optionally substituted, linear or branched $C_1$-$C_6$ alkyl, $R_{17}$ and $R_{18}$, which may be identical or different, representing an optionally substituted, linear or branched $C_1$-$C_6$ alkyl, optionally $R_{17}$ and $R_{18}$ form, together with the nitrogen atom to which they are attached, a saturated, unsaturated or aromatic 5- to 8-membered heterocycle optionally containing one or more other heteroatoms or groups chosen from N, O, S, $S(O)_2$ and/or $C(O)$, the heterocycle being optionally substituted; and/or
  $R_{10}$, $R_{11}$, $R_{12}$, and $R_{13}$ form, in pairs, with adjacent radicals, an optionally substituted, saturated or unsaturated (hetero)cycle;

$R_{14}$ and $R_{15}$, which may be identical or different, represent an atom or group chosen from:
  a hydrogen atom;
  a linear or branched $C_1$-$C_6$ alkyl radical optionally substituted with one or more radicals, which may be identical or different, chosen from hydroxyls, amino, ($C_1$-$C_6$)alkylamino or di($C_1$-$C_6$)alkylamino, ($C_1$-$C_6$)alkylimidazole, mono/di/tri($C_1$-$C_6$)alkylammonium, $An^-$, ($C_1$-$C_6$)alkylimidazolium $An^-$, ($C_1$-$C_6$)alkylpyridinium $An^-$; ($C_1$-$C_6$)alkylpiperidinium, $An^-$; or
  $R_{14}$ and $R_{15}$ form, together with the nitrogen to which they are attached, a cationic or non-cationic 4- to 7-membered heterocycle which may also contain one or more heteroatoms, said heterocycle possibly being substituted with one or more radicals, which may be identical or different, chosen from hydroxyl, amino, (di)($C_1$-$C_6$)alkylamino, $C_1$-$C_6$ alkoxy, mono/di/tri($C_1$-$C_6$)alkylammonium, $An^-$; ($C_1$-$C_6$)alkylimidazolium, $An^-$; ($C_1$-$C_6$)alkylpyridinium, $An^-$; or $C_1$-$C_6$ alkyl;

$R'_{14}$ represents an atom or group chosen from:
  hydrogen;
  linear or branched $C_1$-$C_6$ alkyl which may be substituted with one or more radicals, which may be identical or different, chosen from hydroxyl, amino, ($C_1$-$C_6$)alkylamino or di($C_1$-$C_6$)alkylamino, ($C_1$-$C_6$)alkylimidazole, mono/di/tri($C_1$-$C_6$)alkylammonium $An^-$, ($C_1$-$C_6$)alkylimidazolium $An^-$, ($C_1$-$C_6$)alkylpyridinium $An^-$, ($C_1$-$C_6$)alkylpiperidinium $An^-$;

wherein when the compounds of formula (I) are cationic, then their electro-neutrality is provided by one or more anionic counterions $An^-$; and when $Y_1$ represents NH and $Y_2$ represents a CH group, then X represents a radical (II).

5. The compound of claim 4, wherein X represents an aryl group of formula (II) with:
  Ar represents a substituted aryl group, of which at least one of the substituents $R_8$ represents a radical —$OR'_{14}$ and/or —$NR_{14}R_{15}$, and —$NR_{14}R_{15}$ are in position 4 of said aryl;
  $R_{14}$ and $R_{15}$, which may be identical or different, represent an atom or group chosen from:
    a hydrogen atom;
    a linear or branched $C_1$-$C_6$ alkyl radical which may be substituted with one or more radicals, which may be identical or different, chosen from hydroxyls, amino, ($C_1$-$C_6$)alkylamino or di($C_1$-$C_6$)alkylamino, ($C_1$-$C_6$) alkylimidazole, mono/di/tri($C_1$-$C_6$)alkylammonium, $An^-$, ($C_1$-$C_6$)alkylimidazolium $An^-$, ($C_1$-$C_6$)alkylpyridinium $An^-$; ($C_1$-$C_6$)alkylpiperidinium, $An^-$; or
    $R_{14}$ and $R_{15}$ form, together with the nitrogen to which they are attached, a cationic or non-cationic 4- to 7-membered heterocycle which may also contain one or more heteroatoms, said heterocycle optionally being substituted with one or more radicals, which may be identical or different, chosen from hydroxyl, amino, (di)($C_1$-$C_6$)alkylamino, $C_1$-$C_6$ alkoxy, mono/di/tri($C_1$-$C_6$)alkylammonium, $An^-$; ($C_1$-$C_6$)alkylimidazolium, $An^-$; ($C_1$-$C_6$)alkylpyridinium, $An^-$; or $C_1$-$C_6$ alkyl;

$R'_{14}$ represents an atom or group chosen from:
  hydrogen;
  linear or branched $C_1$-$C_6$ alkyl which may be substituted with one or more radicals, which may be identical or different, chosen from hydroxyl, amino, ($C_1$-$C_6$)alkylamino or di($C_1$-$C_6$)alkylamino, ($C_1$-$C_6$) alkylimidazole, mono/di/tri($C_1$-$C_6$)alkylammonium, $An^-$, ($C_1$-$C_6$)alkylimidazolium $An^-$, ($C_1$-$C_6$)alkylpyridinium $An^-$, ($C_1$-$C_6$)alkylpiperidinium $An^-$.

6. The compound of claim 4, wherein X represents a pyrazolopyridine group of formula (III) with
  $R_9$ representing:
    a radical —$NR'_6R'_7$ with $R'_6$ and $R'_7$, which form, together with the nitrogen atom to which they are attached, a saturated, optionally substituted, optionally cationic, 5- to 8-membered heterocycle, or $R'_6$ and $R'_7$, which may be identical or different, represent:
    a hydrogen atom;
    a $C_1$-$C_{10}$ alkyl radical optionally substituted with one or more groups chosen from i) hydroxyl, ii) optionally substituted, 5- to 8-membered, cationic or non-cationic, saturated, unsaturated or aromatic (hetero)cycle, iii) —$N(R')R"$, iv) —$N+R'R"R'''$ with R', R" and R''' each independently representing a $C_1$-$C_6$ alkyl group;
    or
    a radical —$OR'_6$ with $R'_6$ representing a $C_1$-$C_{10}$ alkyl radical optionally interrupted with one or more non-adjacent heteroatoms, and/or optionally substituted with one or more groups chosen from i) hydroxyl, ii) optionally substituted, 5- to 8-membered, cationic or non-cationic, saturated, unsaturated or aromatic (hetero)cycle, iii) —$N(R')R"$, iv) —$N+R'R"R'''$ with R', R" and R''' each independently representing a $C_1$-$C_6$ alkyl group;

$R_{10}$, $R_{11}$, $R_{12}$ and $R_{13}$, which may be identical or different, represent an atom or group chosen from:
  hydrogen;
  halogen;
  linear or branched $C_1$-$C_6$ alkyl which may be substituted with one or more radicals, which may be identical or different, chosen from hydroxyls, amino, ($C_1$-$C_6$)alkylamino or di($C_1$-$C_6$)alkylamino;
  linear or branched $C_1$-$C_6$ alkoxy which may be substituted with one or more radicals, which may be identical or different, chosen from hydroxyls, amino, ($C_1$-$C_6$)alkylamino or di($C_1$-$C_6$)alkylamino.

7. The compound of claim 1, wherein:

$Z_1$ represents an oxygen atom or a group —N($R_6$)—;

$R_2$, $R_3$, $R_4$ and $R_5$, which may be identical or different, represent an atom or group chosen from:
- hydrogen;
- halogen;
- linear or branched $C_1$-$C_6$ alkyl which may be substituted with one or more radicals, which may be identical or different, chosen from hydroxyls, amino, mono($C_1$-$C_6$)alkylamino or di($C_1$-$C_6$)alkylamino; or
- linear or branched $C_1$-$C_6$ alkoxy which may be substituted with one or more radicals, which may be identical or different, chosen from hydroxyls, amino, mono($C_1$-$C_6$)alkylamino or di($C_1$-$C_6$)alkylamino;

$R_1$, $R_6$, $R'_6$, and $R'_7$, which may be identical or different, represent an atom or group chosen from:
- a hydrogen atom;
- a linear or branched $C_1$-$C_6$ alkyl radical which may be substituted with one or more radicals, which may be identical or different, chosen from a) hydroxyls; b) amino; c) ($C_1$-$C_6$)alkylamino; d) di($C_1$-$C_6$)alkylamino; e) ($C_1$-$C_6$)alkylimidazolyl; f) mono/di/tri ($C_1$-$C_6$)alkylammonium, An⁻; g) ($C_1$-$C_6$)alkylimidazolium, An⁻; h) ($C_1$-$C_6$)alkylpyridinium, An⁻; i) ($C_1$-$C_6$)alkylpiperidinium, An⁻; j) (di)($C_1$-$C_6$)alkylpiperazinium, An⁻; k) morpholino and l) ($C_1$-$C_6$)alkylmorpholinium;

X represents a radical of formula (II') or of formula (III):

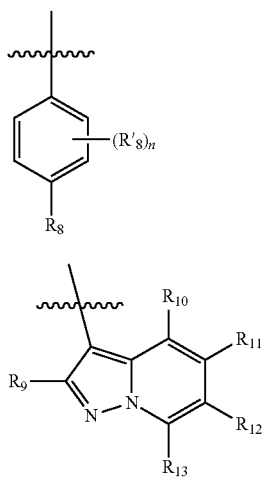

in which formulae (II') and (III):

∿∿∿ corresponds to the point of anchorage of the group (II) or (III) to the rest of the molecule;

n represents an integer between 0 and 4; when n is greater than or equal to 2, then the radicals $R'_8$ may be identical or different;

$R'_8$ represents an atom or group chosen from:
1) halogen; 2) $C_1$-$C_6$ alkyl, optionally substituted with one or more radicals chosen from the radicals i) hydroxyl, ii) $C_1$-$C_2$ alkoxy, iii) (poly)hydroxy($C_2$-$C_4$)alkoxy, iv) acylamino, v) amino substituted with one or two identical or different $C_1$-$C_4$ alkyl radicals, optionally bearing at least one hydroxyl group, or the two radicals being able to form, with the nitrogen atom to which they are attached, a saturated or unsaturated heterocycle comprising from 5 to 7 members, optionally comprising another heteroatom identical to or different than nitrogen, vi) halogen; vii) cationic or non-cationic heterocycle, —$C_1$-$C_6$ alkylpyridinium An⁻, $C_1$-$C_6$ alkylpiperidinium An⁻; viii) $C_1$-$C_6$ mono/di/trialkylammonium; 3) hydroxyl; 4) $C_1$-$C_6$ alkoxy optionally substituted with one or more identical or different radicals chosen from i) hydroxyl; ii) amino, iii) $C_1$-$C_6$ mono- or dialkylamino; iv) ($C_1$-$C_6$)alkylimidazole; v) mono/di/tri ($C_1$-$C_6$)alkylammonium; vi) ($C_1$-$C_6$)alkylimidazolium An⁻; vii) ($C_1$-$C_6$)alkylpyridinium An⁻; viii) ($C_1$-$C_6$)alkylpiperidinium An⁻; 5) $C_1$-$C_6$ alkoxycarbonyl; 6) $C_1$-$C_6$ alkylcarbonyloxy; 7) (poly)hydroxy($C_2$-$C_4$)alkoxy; 8) amino; 9) 5- or 6-membered heterocycloalkyl; 10) optionally cationic 5- or 6-membered heteroaryl optionally substituted with a $C_1$-$C_4$ alkyl radical; 11) amino substituted with one or two identical or different $C_1$-$C_6$ alkyl radicals optionally bearing at least i) hydroxyl, ii) amino optionally substituted with one or two $C_1$-$C_3$ alkyl radicals, said alkyl radicals possibly forming, with the nitrogen atom to which they are attached, a saturated or unsaturated heterocycle comprising from 5 to 7 members, optionally comprising at least one other heteroatom different than or identical to nitrogen, iii) quaternary ammonium —N+R'R"R'", M⁻ for which R', R" and R'", which may be identical or different, represent a hydrogen atom or a $C_1$-$C_4$ alkyl group; and M⁻ represents an anionic counterion, iv) optionally cationic 5- or 6-membered heteroaryl, optionally substituted with a $C_1$-$C_4$ alkyl radical; 12) quaternary ammonium —N⁺R'R"R'", M⁻ for which R', R", R'" and M⁻ are as defined previously; 13) acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; 14) carbamoyl ((R)$_2$N—C(O)—) in which the radicals R, which may be identical or different, represent a hydrogen atom or a $C_1$-$C_4$ alkyl radical optionally bearing at least one hydroxyl group; 15) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical or a phenyl radical; 16) aminosulfonyl ((R)$_2$N—S(O)$_2$—) in which the radicals R, which may be identical or different, represent a hydrogen atom or a $C_1$-$C_4$ alkyl radical optionally bearing at least one hydroxyl group; 17) carboxyl in acid or salified form; 18) cyano; 19) nitro; 20) polyhaloalkyl; 21) carboxyl; 22) phenylcarbonyloxy optionally substituted with one or more hydroxyl groups; 23) phenyloxycarbonyl optionally substituted with one or more hydroxyl groups; 24) phenyl optionally substituted with one or more hydroxyl or alkoxy groups; and 25) phenoxy; or when n is greater than or equal to 2, two contiguous radicals $R'_8$ form, together with the carbon atoms which bear them, an optionally substituted (hetero)cycle;

$R_8$ represents an atom or group chosen from:
- hydrogen;
- halogen;
- —$OR'_{14}$;
- —$NR_{14}R_{16}$;
- $C_1$-$C_6$ alkyl optionally substituted with one or more radicals, which may be identical or different, chosen from hydroxyls, amino, $C_1$-$C_6$ monoalkylamino or dialkylamino, halogen, $C_1$-$C_6$ alkylimidazole, $C_1$-$C_6$ trialkylammonium An$^-$, $C_1$-$C_6$alkylimidazolium An$^-$, $C_1$-$C_6$ alkylpyridinium An$^-$,$C_1$-$C_6$alkylpiperidinium An$^-$;

carboxyl (—$CO_2H$);

carboxamide (—$CO_2NH_2$);

$R_9$ represents
- a radical —$OR'_6$; or
- a radical —$NR'_6R'_7$;

$R_{10}$, $R_{11}$, $R_{12}$ and $R_{13}$, which may be identical or different, represent an atom or group chosen from:
- hydrogen;
- halogen;
- linear or branched $C_1$-$C_6$ alkyl which may be substituted with one or more radicals, which may be identical or different, chosen from hydroxyls, amino, ($C_1$-$C_6$)alkylamino or di($C_1$-$C_6$)alkylamino; or
- linear or branched $C_1$-$C_6$ alkoxy which may be substituted with one or more radicals, which may be identical or different, chosen from hydroxyls, amino, ($C_1$-$C_6$)alkylamino or di($C_1$-$C_6$)alkylamino;

$R_{14}$ and $R_{15}$, which may be identical or different, represent an atom or group chosen from:
- a hydrogen atom;
- a linear or branched $C_1$-$C_6$ alkyl radical optionally substituted with one or more radicals, which may be identical or different, chosen from hydroxyls, amino, ($C_1$-$C_6$)alkylamino or di($C_1$-$C_6$)alkylamino, ($C_1$-$C_6$) alkylimidazole, mono/di/tri($C_1$-$C_6$)alkylammonium, An$^-$; ($C_1$-$C_6$)alkylimidazolium An$^-$; ($C_1$-$C_6$)alkylpyridinium An$^-$; ($C_1$-$C_6$)alkylpiperidinium, An$^-$; or
- $R_{14}$ and $R_{15}$ form, together with the nitrogen to which they are attached, a cationic or non-cationic 4- to 7-membered heterocycle which may also contain one or more heteroatoms, said heterocycle possibly being substituted with one or more radicals, which may be identical or different, chosen from hydroxyl, amino, (di)($C_1$-$C_6$)alkylamino, $C_1$-$C_6$ alkoxy, mono/ di/tri($C_1$-$C_6$)alkylammonium, An$^-$; ($C_1$-$C_6$)alkylimidazolium, An$^-$; ($C_1$-$C_6$)alkylpyridinium, An$^-$; or $C_1$-$C_6$ alkyl;

$R'_{14}$ represents an atom or group chosen from:
- hydrogen;
- linear or branched $C_1$-$C_6$ alkyl optionally substituted with one or more radicals, which may be identical or different, chosen from hydroxyl, amino, ($C_1$-$C_6$) alkylamino or di($C_1$-$C_6$)alkylamino, ($C_1$-$C_6$)alkylimidazole, mono/di/tri($C_1$-$C_6$)alkylammonium, An$^-$, ($C_1$-$C_6$)alkylimidazolium An$^-$, ($C_1$-$C_6$)alkylpyridinium An$^-$, ($C_1$-$C_6$)alkylpiperidinium An$^-$;

it being understood that:
- when the compounds of formula (I) are cationic, then their electro-neutrality is provided by one or more cosmetically acceptable anionic counterion anions, which may be identical or different; and
- when $Y_1$ represents NH and $Y_2$ represents a CH group, then X represents a radical (II) or (II').

8. The compound of claim 7, wherein X represents an aryl group of formula (II) or (II') with $R_8$ representing a radical —$NR_{14}R_{15}$; wherein $R_{14}$ represents an atom or group chosen from i) hydrogen, and ii) ($C_1$-$C_4$)alkyl optionally substituted with one or more hydroxyl groups, and $R_{15}$ represents an atom or group chosen from i) hydrogen, and ii) ($C_1$-$C_6$)alkyl optionally substituted with one or more hydroxyl groups, or a heterocycle.

9. The compound of claim 4, wherein $Z_1$ represents a radical —$N(R_6)$— and X represents a radical (III) with $R_9$ representing a group —$N(R'_6)$—$R'_7$ in which $R_1$ and $R_6$ and/or $R'_6$ and $R'_7$ form, together with the nitrogen atom which bears them, a cationic or non-cationic heterocycle chosen from piperazinyl, piperazinium, imidazolyl, pyrrolidinyl, pyridinyl, morpholinyl, morpholinium, piperidinyl, or piperidinium.

10. The compound of claim 7, wherein $Z_1$ represents a radical —$N(R_6)$— and X represents a radical (II) or (II') with $R_1$ and $R_6$ representing a cationic or non-cationic heterocycle.

11. The compound of claim 4, wherein the radicals $R_1$, $R_6$ and $R'_6$ are independently chosen from a hydrogen atom, a $C_1$-$C_6$ alkyl radical or a $C_1$-$C_6$ alkyl radical substituted with one or more hydroxyl groups.

12. The compound of claim 1, wherein the azomethine dyes comprise two symmetrical pyrazolopyridine units of formulae (I') below, and also the leuco forms, optical isomers, geometrical isomers and tautomers thereof, the acid or base addition salts thereof and the solvates thereof:

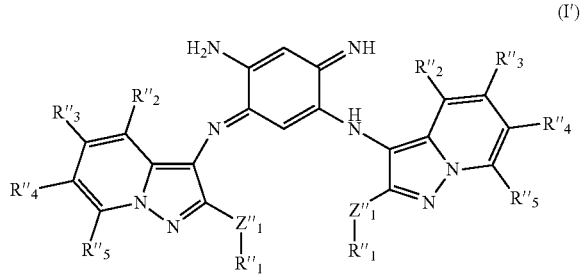

in which formula (I'):

$Z''_1$ is independently chosen from an oxygen atom or a group —$N(R''_6)$—;

when $Z''_1$ represents —$N(R''_6)$— then $R''_1$ and $R''_6$ may form, together with the nitrogen atom to which they are attached, a cationic or non-cationic, saturated, optionally unsaturated, heterocycle comprising 5 or 6 members, optionally substituted with one or more ($C_1$-$C_4$)alkyl groups;

$R''_1$ is independently chosen from a $C_1$-$C_6$ alkyl radical, optionally interrupted with one or more non-adjacent oxygen atoms, and/or optionally substituted with:
- a hydroxyl radical,
- a di($C_1$-$C_4$)alkylamino radical,
- a heterocycle optionally substituted with one or more $C_1$-$C_4$ alkyl and/or hydroxyl radicals and chosen from pyrrolidine, piperidine, morpholine, piperazine and imidazole;

$R''_6$ is independently chosen from:
- a hydrogen atom,
- a $C_1$-$C_{10}$ alkyl radical optionally substituted with a hydroxyl radical;

$R''_2$, $R''_3$, $R''_4$, and $R''_5$ are each independently chosen from:
- a hydrogen atom,
- a $C_1$-$C_4$ alkyl radical.

13. The compound of claim 1, wherein said compound is chosen from:

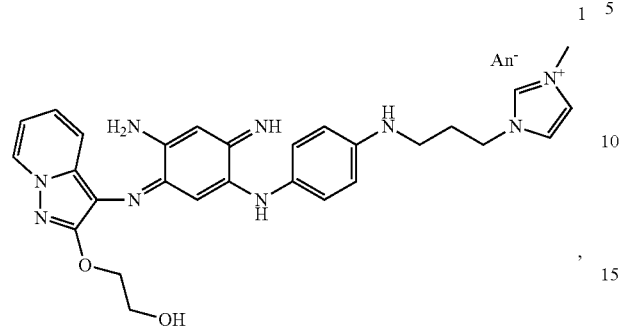

3-[3-(4-{4-Amino-3-[2-(2-hydroxyethoxy)pyrazolo[1,5-a]pyridin-3-ylimino]-6-iminocyclohexa-1,4-dienylamino}phenylamino)propyl]-1-methyl-3H-imidazol-1-ium

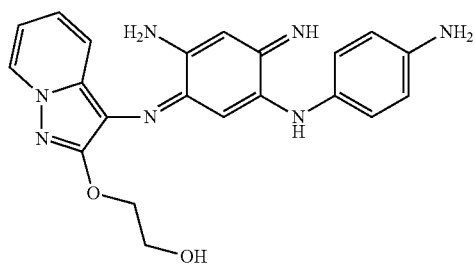

2-{3-[2-Amino-5-(4-aminophenylamino)-4-iminocyclohexa-2,5-dienylideneamino]pyrazolo[1,5-a]pyridin-2-yloxy}ethanol

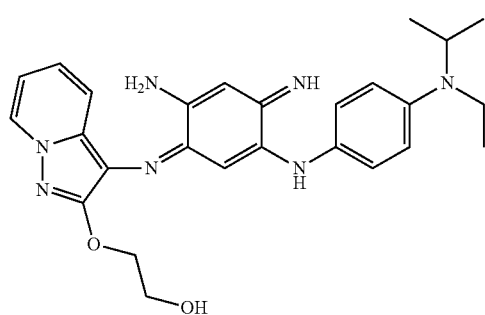

2-{3-[2-Amino-5-(4-ethylisopropylamino)phenylamino]-4-iminocyclohexa-2,5-dienylideneamino]pyrazolo[1,5-a]pyridin-2-yloxy}ethanol

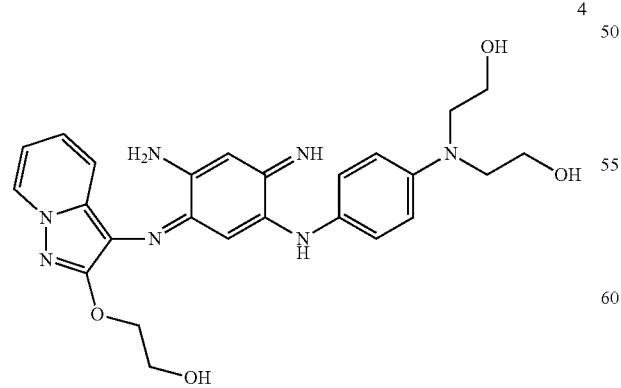

2-{3-[2-Amino-5-{4-[bis(2-hydroxyethyl)amino]phenylamino}-4-iminocyclohexa-2,5-dienylideneamino]pyrazolo[1,5-a]pyridin-2-yloxy}ethanol

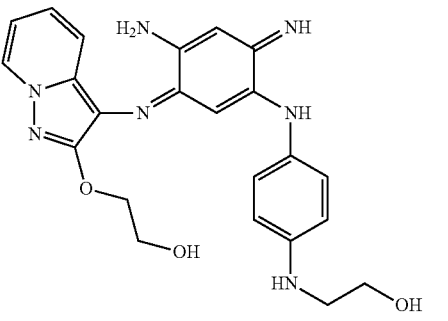

2-{3-[2-Amino-5-[4-(2-hydroxyethylamino)phenylamino]4-iminocyclohexa-2,5-dienylideneamino]pyrazolo[1,5-a]pyridin-2-yloxy}ethanol

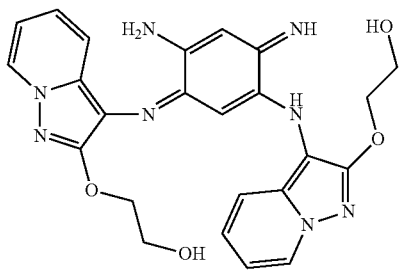

2-{3-[2-Amino-5-[2-(2-hydroxyethoxy)pyrazolo[1,5-a]pyridin-3-ylamino]-4-iminocyclohexa-2,5-dienylideneamino]pyrzolo[1,5-a]-pyridin-2-yloxy}ethanol

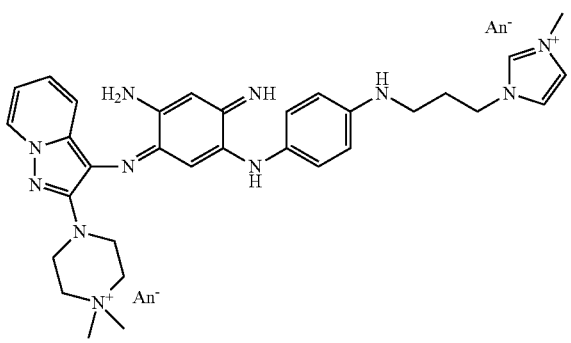

4-[3-({(2-amino-4-imino-5-[(4-{[3-(3-methyl-1H-imidazol-3-ium-1-yl)propyl]amino}phenyl)amino]cyclohexa-2,5-dien-1-ylidene}amino)pyrazolo[1,5-a]pyridin-2-yl]-1,1-dimethylpiperazin-1-ium, An⁻

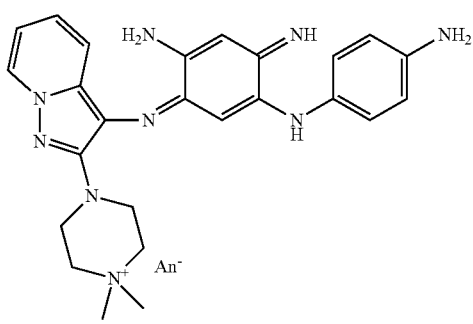

4-{3-[2-Amino-5-(4-aminophenylamino)-4-iminocyclohexa-2,5-dienylideneamino]pyrazolo[1.5-a]pyridin-2-yl}-1,1-dimethylpiperazin-1-ium, An⁻

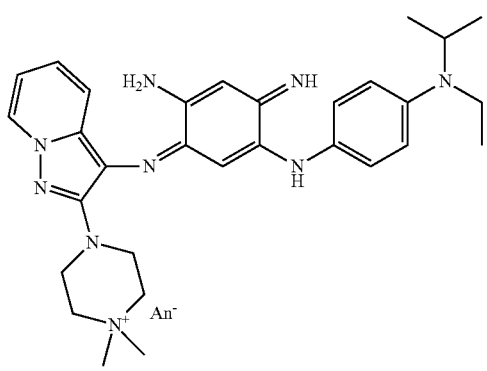

4-{3-[2-Amino-5-[4-(ethylisopropylamino)phenylamino]-4-iminocyclohexa-2,5-dienylideneamino]pyrazolo[1,5-a]pyridin-2-yl}-1,1-dimethylpiperazin-1-ium, An⁻

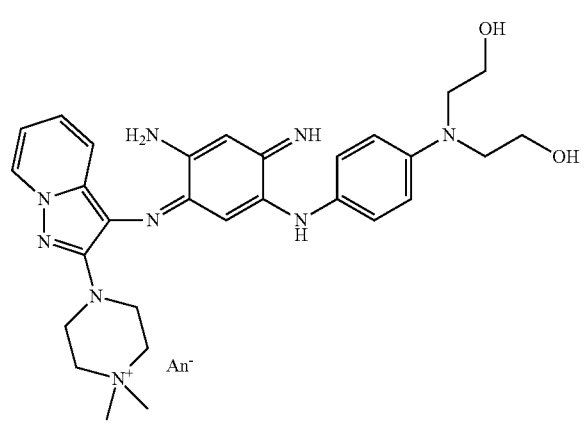

4-{3-[2-Amino-5-{4-[bis(2-hydroxyethyl)amino]phenylamino}-4-iminocyclohexa-2,5-dienylideneamino]pyrazolo[1,5-a]pyridin-2-yl}-1,1-dimethylpiperazin-1-ium, An⁻

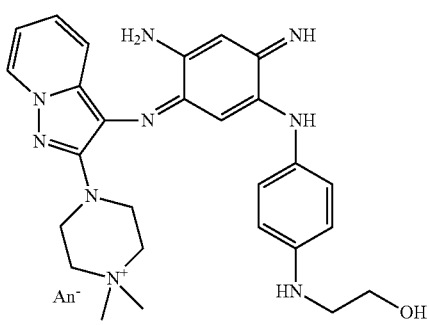

4-{3-[2-Amino-5-[4-(2-hydroxyethylamino)phenylamino]-4-iminocyclohexa-2,5-dienylideneamino]pyrazolo[1,5-a]pyridin-2-yl}-1,1-dimethylpiperazin-1-ium, An⁻

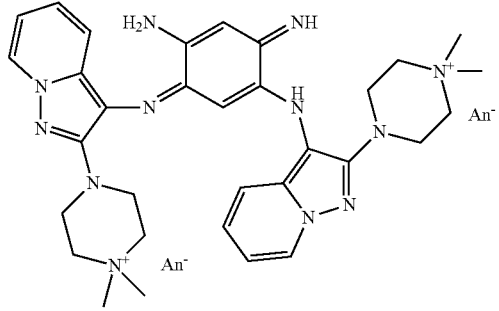

4-(3-{[(2-amino-5-{[2-(4,4-dimethylpiperazin-4-ium-1-yl)pyrazolo[1,5-a]pyridin-3-yl]amino}-4-iminocyclohexa-2,5-dien-1-ylidene]amino}pyrazolo[1,5-a]pyridin-2-yl)-1,1-dimethylpiperazin-1-ium, An⁻ and also the organic or mineral acid or base addition salts thereof, the leuco forms thereof, the geometrical isomers thereof, the tautomers thereof, the solvates thereof, and the hydrates thereof, with An⁻, which may be identical or different, representing an anionic counterion.

14. A cosmetic composition comprising at least one compound of claim 1.

15. A method for dyeing keratin fibers, comprising applying to keratin fibers a compound chosen from azomethine dyes comprising at least one pyrazolopyridine unit of formulae (I), a leuco form, an optical isomer, a geometrical isomer, a tautomers thereof, an organic or mineral acid or base addition salt thereof, a solvate thereof, or a hydrate thereof:

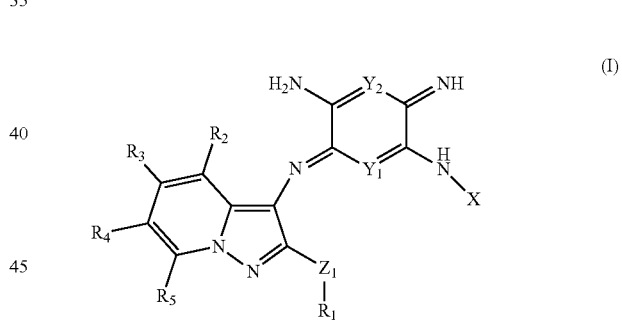

(I)

in which formula (I):
$Y_1$ and $Y_2$, which may be identical or different, represent a nitrogen atom or a group C(R) with R representing a hydrogen atom or a (C₁-C₆)alkyl group;
$Z_1$ represents an oxygen atom or a group —N(R₆)—; when $Z_1$ represents —N(R₆)—, then $R_1$ and $R_6$ optionally form, together with the nitrogen atom to which they are attached, an optionally substituted, optionally cationic, 5- to 8-membered, saturated, unsaturated or aromatic heterocycle;
$R_1$ and $R_6$, which may be identical or different, represent:
a hydrogen atom;
a C₁-C₁₀ alkyl radical optionally interrupted with one or more non-adjacent heteroatoms, and/or optionally substituted;
an optionally substituted, 5- to 8-membered, cationic or non-cationic, saturated, unsaturated or aromatic (hetero)cyclic radical;

$R_2$, $R_3$, $R_4$, and $R_5$, which may be identical or different, each independently represent:
a hydrogen atom;
an optionally substituted $C_1$-$C_6$ alkyl radical;
a group chosen from —$NH_2$, —$N(H)R_{10}$, —$N(R_{11})R_{12}$, OH and/or —$OR_9$, with $R_9$ and $R_{10}$ representing an optionally substituted, linear or branched $C_1$-$C_6$ alkyl, $R_{11}$ and $R_{12}$, which may be identical or different, representing an optionally substituted, linear or branched $C_1$-$C_6$ alkyl, wherein $R_{11}$ and $R_{12}$ optionally form, together with the nitrogen atom to which they are attached, a saturated, unsaturated or aromatic 5- to 8-membered heterocycle optionally containing one or more other heteroatoms or groups chosen from N, O, S, $S(O)_2$ and C(O), the heterocycle being optionally substituted;
a halide and/or
$R_2$, $R_3$, $R_4$, and $R_5$ form, in pairs, with adjacent radicals, an optionally substituted, saturated or unsaturated (hetero)cycle;
X represents an optionally substituted aryl or optionally substituted heteroaryl radical;
wherein
when the compounds of formula (I) are cationic, then their electro-neutrality is provided by one or more cosmetically acceptable anions which may be identical or different; and
when $Y_1$ represents NH and $Y_2$ represents a CH group, then X represents a group other than a pyrazolo[1,5-a]pyridin-3-yl group which is optionally substituted.

16. A process for preparing the compounds of claim 1, wherein formula (I) is symmetrical, comprising:
starting from reagent $A_2$ of 3,4-diamino type:

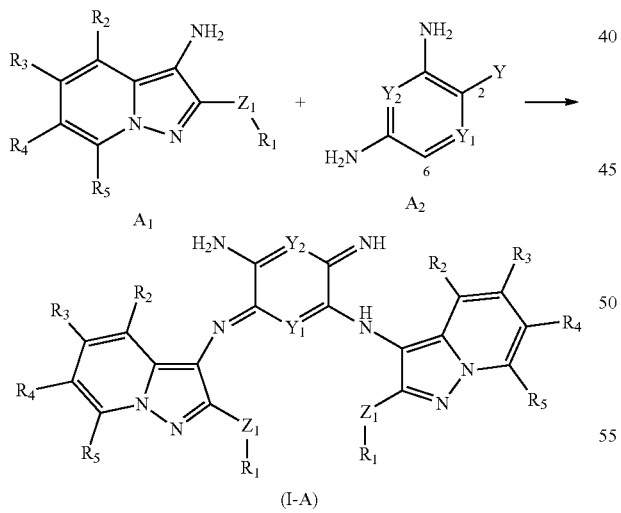

reacting at least two molar equivalents of pyrazolo[1,5-a]pyridine compound $A_1$ comprising an amino group in position 3 with a reagent $A_2$ which is free in position 6 of the aromatic ring and comprising in position 2 a radical Y which is either a hydrogen atom or an electrofugal group, then
maintaining the reaction medium under stirring for a time of between 5 minutes and 48 hours; and then
optionally purifying reaction products (I-A);
wherein in formulae $A_1$, $A_2$ and (I-A), the radicals $R_1$, $Z_1$, $R_2$, $R_3$, $R_4$, $R_5$, $Y_1$ and $Y_2$ are as defined previously and that, when $Y_1$ represents NH then $Y_2$ cannot represent a CH group and Y represents a hydrogen atom or an electrofugal atom or group.

17. A process for preparing the compounds of claim 1, wherein formula (I) is symmetrical, comprising:
starting from reagent $A_4$ of 3,4-dinitro type:

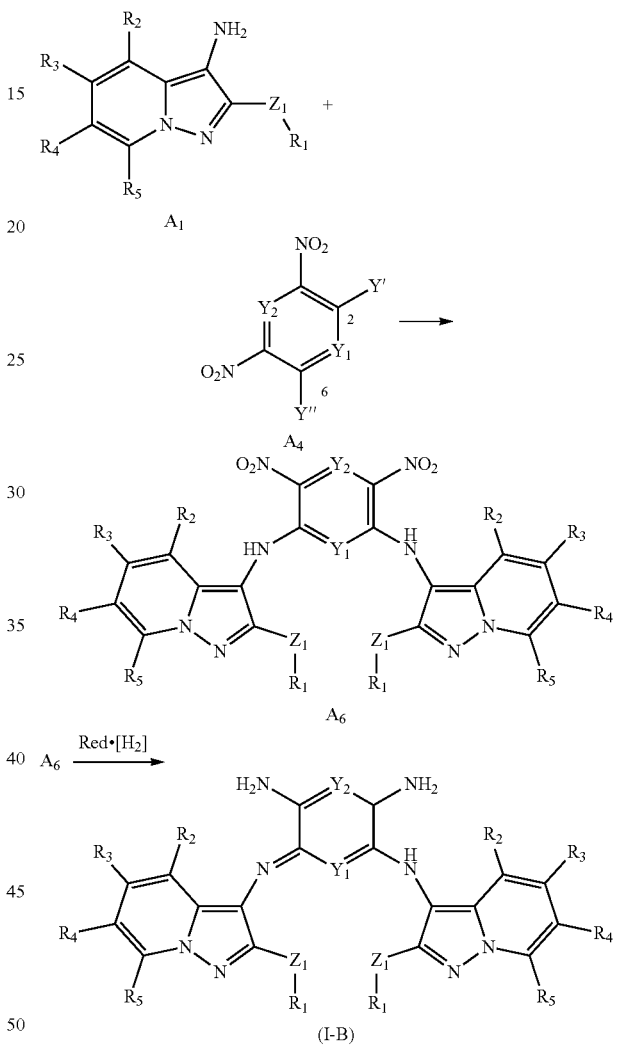

reacting at least two molar equivalents of pyrazolo[1,5-a]pyridine compound Ai comprising an amino group in position 3 with a reagent $A_4$ comprising in position 2 and 6 of the aromatic ring an electrofugal atom or group; then
maintaining the reaction medium under stirring for a time of between 5 minutes and 48 hours; then
optionally purifying the reaction product $A_6$;
reducing $A_5$
optionally purifying compound 1;
wherein $R_1$, $Z_1$, $R_2$, $R_3$, $R_4$, $R_5$, X, Y, $Y_1$ and $Y_2$ are as defined previously, and Y' and Y", which may be identical or different, represent an electrofugal atom or group; and that, when $Y_1$ represents NH then $Y_2$ does not represent a CH group.

18. A process for preparing compounds of claim 1, wherein formula (I) is symmetrical or dissymmetrical, comprising:

starting from reagent $A_2$ of 3,4-diamino type:

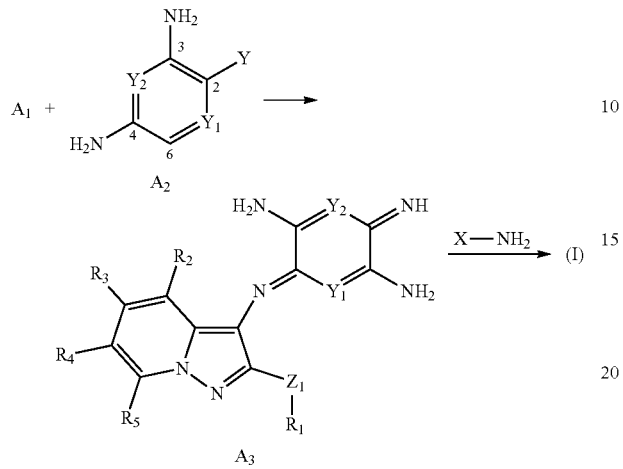

reacting one molar equivalent of pyrazolo[1,5-a]pyridine compound Ai comprising an amino group in position 3 with a reagent $A_2$ as defined previously; then maintaining the reaction medium under stirring for a time of between 5 minutes and 48 hours, and then optionally purifying the reaction product $A_3$;

reacting compound $A_3$ with one molar equivalent of a reagent bearing a (hetero)aryl group comprising a primary amine X—$NH_2$ under the same conditions as steps 1) and 2), optionally purifying a compound of formula (I);

wherein $R_1$, $Z_1$, $R_2$, $R_3$, $R_4$, $R_5$, X, Y, $Y_1$ and $Y_2$ are as defined previously, Y' and Y" represent an atom or group and that, when $Y_1$ represents NH and $Y_2$ represents a CH group, then X represents a group other than a pyrazolo[1,5-a]pyridin-3-yl group which is optionally substituted.

19. A process for preparing compounds of claim 1, wherein formula (I) is symmetrical or dissymmetrical, comprising:

starting from reagent $A_4$ of 3,4-dinitro type:

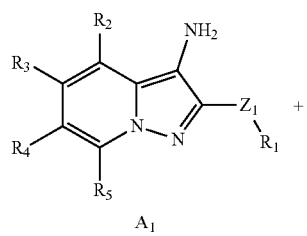

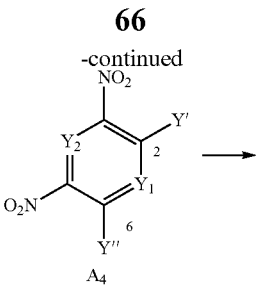

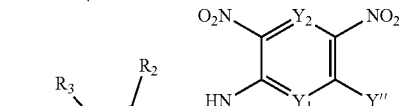

reacting one molar equivalent of pyrazolo[1,5-a]pyridine compound Ai comprising an amino group in position 3 with a reagent $A_4$ comprising in position 2 and 6 of the aromatic ring an electrofugal atom or group; then maintaining the reaction medium under stirring for a time of between 5 minutes and 48 hours, and then optionally purifying the reaction product $A_5$; then reacting compound $A_5$ with one molar equivalent of a reagent bearing a (hetero)aryl group comprising a primary amine X—$NH_2$ in a polar aprotic heteroaromatic solvent; then optionally reducing $A'_6$ to give a compound of formula (I);

wherein $R_1$, $Z_1$, $R_2$, $R_3$, $R_4$, $R_5$, X, Y, $Y_1$ and $Y_2$ are as defined previously, and Y' and Y", which may be identical or different, represent an electrofugal atom or group;

and wherein $Y_1$ represents NH and $Y_2$ represents a CH group, then X represents a group other than a pyrazolo[1,5-a]pyridin-3-yl group which is optionally substituted.

20. A multi-compartment device or kit, comprising, in at least one of the compartments, the compound of claim 1.

UNITED STATES PATENT AND TRADEMARK OFFICE
CERTIFICATE OF CORRECTION

PATENT NO. : 10,731,038 B2
APPLICATION NO. : 16/309296
DATED : August 4, 2020
INVENTOR(S) : Stéphane Sabelle et al.

Page 1 of 1

It is certified that error appears in the above-identified patent and that said Letters Patent is hereby corrected as shown below:

In the Claims

Claim 4, Column 52, Line 49, change "-OR's" to -- -OR'6 --.

Claim 6, Column 54, Line 54, change "R''" (second occurrence) to -- R''' --.

Claim 7, Column 56, Line 65, change "R16" to -- R 15 --.

Claim 17, Column 64, Line 54, change "Ai" to -- A1 --.

Signed and Sealed this
Nineteenth Day of January, 2021

Andrei Iancu
*Director of the United States Patent and Trademark Office*